(12) United States Patent
Goericke et al.

(10) Patent No.: US 11,819,361 B2
(45) Date of Patent: Nov. 21, 2023

(54) SPLIT ELECTRODE DESIGN FOR A TRANSDUCER

(71) Applicant: InvenSense, Inc., San Jose, CA (US)

(72) Inventors: Fabian T. Goericke, Berkeley, CA (US); Richard J. Przybyla, Piedmont, CA (US); Benjamin E. Eovino, Oakland, CA (US)

(73) Assignee: InvenSense, Inc., San Jose, CA (US)

( * ) Notice: Subject to any disclaimer, the term of this patent is extended or adjusted under 35 U.S.C. 154(b) by 461 days.

(21) Appl. No.: 16/870,929

(22) Filed: May 9, 2020

(65) Prior Publication Data

US 2021/0177378 A1 Jun. 17, 2021

Related U.S. Application Data

(60) Provisional application No. 62/947,558, filed on Dec. 13, 2019.

(51) Int. Cl.
| | |
|---|---|
| *G01S 7/521* | (2006.01) |
| *G01N 29/24* | (2006.01) |
| *B06B 1/06* | (2006.01) |
| *H10N 30/87* | (2023.01) |
| *A61B 8/00* | (2006.01) |

(52) U.S. Cl.
CPC .......... *A61B 8/4483* (2013.01); *B06B 1/0688* (2013.01); *G01N 29/2437* (2013.01); *G01S 7/521* (2013.01); *H10N 30/87* (2023.02)

(58) Field of Classification Search
CPC ............. A61B 8/4483; B06B 1/0688; G01N 29/2437; G01S 7/521; H01L 41/047
See application file for complete search history.

(56) References Cited

U.S. PATENT DOCUMENTS

| | | | | |
|---|---|---|---|---|
| 4,527,433 A | * | 7/1985 | Gutterman | G01F 1/667 73/861.28 |
| 6,547,788 B1 | * | 4/2003 | Maguire | A61N 7/02 606/49 |
| 2008/0122320 A1 | * | 5/2008 | Fazzio | H04R 17/02 310/366 |

(Continued)

FOREIGN PATENT DOCUMENTS

WO WO-2019099681 A1 * 5/2019 ........... A61B 8/4236

*Primary Examiner* — Isam A Alsomiri
*Assistant Examiner* — Joseph C Fritchman

(57) ABSTRACT

An ultrasonic transducer device comprises a piezoelectric micromachined ultrasonic transducer (PMUT), a transmitter with first and second differential outputs, and a controller. The PMUT includes a membrane layer. A bottom electrode layer, comprising a first bottom electrode and a second bottom electrode, is disposed above the membrane layer. The piezoelectric layer is disposed above the bottom electrode layer. The top electrode layer is disposed above the piezoelectric layer and comprises a segmented center electrode disposed above a center of the membrane layer and a segmented outer electrode spaced apart from the segmented center electrode. The controller, responsive to the PMUT being placed in a transmit mode, is configured to couple the first and second segments of the bottom electrode layer with ground, couple the first output of the transmitter with the segments of the segmented center electrode, and couple the second output with the segments of the segmented outer electrode.

18 Claims, 12 Drawing Sheets

(56) References Cited

U.S. PATENT DOCUMENTS

| | | | |
|---|---|---|---|
| 2010/0117485 A1* | 5/2010 | Martin | H04R 17/02 |
| | | | 310/319 |
| 2016/0107194 A1* | 4/2016 | Panchawagh | G01S 15/8915 |
| | | | 310/317 |
| 2017/0021391 A1* | 1/2017 | Guedes | B06B 1/0603 |
| 2017/0320093 A1* | 11/2017 | Chatterjee | H01L 41/0973 |
| 2018/0154394 A1* | 6/2018 | Haque | H01L 41/053 |

* cited by examiner

SECTION A-A

SPLIT ELECTRODE DESIGN FOR A TRANSDUCER

CROSS-REFERENCE TO RELATED APPLICATION—PROVISIONAL

This application claims priority to and benefit of U.S. Provisional Patent Application No. 62/947,558 filed on Dec. 13, 2019 entitled "SPLIT ELECTRODE DESIGN FOR A TRANSDUCER" by Fabian T. Goericke et al., and assigned to the assignee of the present application, the disclosure of which is hereby incorporated herein by reference in its entirety.

BACKGROUND

A variety of devices exist which utilize sonic sensors (e.g., sonic emitters and receivers, or sonic transducers). By way of example, and not of limitation, a device may utilize one or more sonic sensors to track the location of the device in space, to detect the presence of objects in the environment of the device, and/or to avoid objects in the environment of the device. Such sonic sensors include transmitters which transmit sonic signals, receivers which receive sonic signals, and transducers which both transmit sonic signals and receive sonic signals. Piezoelectric Micromachined Ultrasonic Transducers (PMUTs), which may be air-coupled, are one type of sonic transducer, which operates in the ultrasonic range, and can be used for a large variety of sensing applications such as, but not limited to: virtual reality controller tracking, presence detection, and object avoidance for drones or other machines, etc.

BRIEF DESCRIPTION OF DRAWINGS

The accompanying drawings, which are incorporated in and form a part of the Description of Embodiments, illustrate various embodiments of the subject matter and, together with the Description of Embodiments, serve to explain principles of the subject matter discussed below. Unless specifically noted, the drawings referred to in this Brief Description of Drawings should be understood as not being drawn to scale. Herein, like items are labeled with like item numbers.

DESCRIPTION OF EMBODIMENTS

Figure 1A:
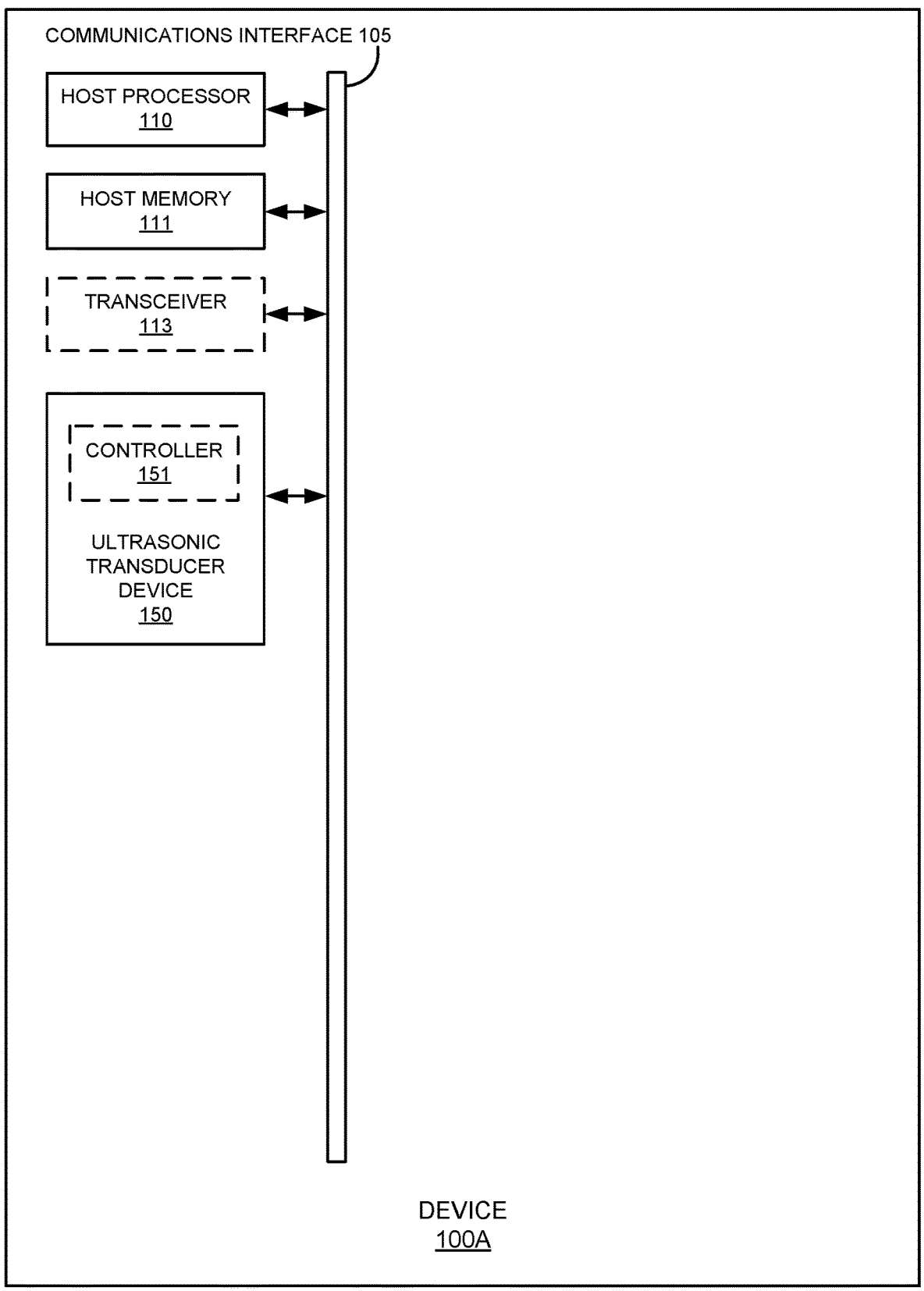
FIGS. 1A and 1B show example block diagrams of some aspects of a device, in accordance with various embodiments.

Reference will now be made in detail to various embodiments of the subject matter, examples of which are illustrated in the accompanying drawings. While various embodiments are discussed herein, it will be understood that they are not intended to limit to these embodiments. On the contrary, the presented embodiments are intended to cover alternatives, modifications and equivalents, which may be included within the spirit and scope of the various embodiments as defined by the appended claims. Furthermore, in this Description of Embodiments, numerous specific details are set forth in order to provide a thorough understanding of embodiments of the present subject matter. However, embodiments may be practiced without these specific details. In other instances, well known methods, procedures, components, and circuits have not been described in detail as not to unnecessarily obscure aspects of the described embodiments.

Overview of Discussion

Air-coupled Piezoelectric Micromachined Ultrasonic Transducers (PMUTs), transmitters, and receivers can be used for a large variety of sensing applications. Conventionally, however, the application field for such PMUT sensing devices is limited by the maximum operating range, which in turn is limited by the strength of the transmitted signal (Tx) and the ability to resolve the received signal (Rx). Any significant improvement to either Tx or Rx could enable longer sensing ranges and thus new applications. The technology described herein presents improvements to both the Tx and the Rx functions and can be used in transmitting devices, receiving devices, and transducers. Conventional air-coupled PMUTs accomplish Tx and Rx with a single electrode in the center of a circular membrane. The signal-to-noise ratio (SNR) of conventional air-coupled PMUTs is limited due to their small size and the presence of interfering sonic signals from the environment.

The new technology described herein utilizes both a center electrode and a ring/outer electrode and splits them both into multiple sections. This new technology may be referred to more specifically as a split electrode design and provides for differential Tx which is stronger than conventional Tx and/or stacked-differential Rx which is more sensitive than conventional Rx. Stronger Tx and more sensitive Rx each improve the signal-to-noise ratio (SNR) and enable longer sensing ranges. Utilizing the split electrode design allows for stronger transmission from the PMUT and/or more sensitive receiving by the PMUT.

Discussion begins with a description of notation and nomenclature. Discussion then shifts to description of some block diagrams of example components of some example devices which may utilize a PMUT of the type described herein. The device may be any type of device which utilizes sonic sensing, for example any device which uses conventional PMUTs could utilize the new PMUTs described herein. Moreover, because of the improved Tx and Rx, many devices which cannot utilize conventional PMUTs due to their limitations may utilize the PMUTs described herein. Some example depictions of a PMUT are described. Utilization of an example PMUT for transmitting signals and for receiving signals is described. Discussion then moves to description of an example ultrasonic sensing device which includes a PMUT of the type described herein. Operation of the example ultrasonic sensing device for transmitting signals and receiving signals is then described. Finally, some example methods of manufacture of a PMUT, of the type described herein, are described.

Notation and Nomenclature

Some portions of the detailed descriptions which follow are presented in terms of procedures, logic blocks, processes, modules and other symbolic representations of operations on data bits within a computer memory. These descriptions and representations are the means used by those skilled in the data processing arts to most effectively convey the substance of their work to others skilled in the art. In the present application, a procedure, logic block, process, module, or the like, is conceived to be one or more self-consistent procedures or instructions leading to a desired result. The procedures are those requiring physical manipulations of physical quantities. Usually, although not necessarily, these quantities take the form of electrical or magnetic signals capable of being stored, transferred, combined, compared, and otherwise manipulated in an electronic device/component.

It should be borne in mind, however, that all of these and similar terms are to be associated with the appropriate physical quantities and are merely convenient labels applied to these quantities. Unless specifically stated otherwise as apparent from the following discussions, it is appreciated that throughout the description of embodiments, discussions utilizing terms such as "electrically coupling," "generating," "processing," "decoupling," "coupling," "switching" or the like, may refer to the actions and processes of an electronic device or component such as: a host processor, a sensor processing unit, a sensor processor, a controller or other processor, a memory, some combination thereof, or the like; and/or a component such as a switch or an emitter, receiver, or transducer operating under control of a host processor, a sensor processing unit, a sensor processor, a controller or other processor, or the like. The electronic device/component manipulates and transforms data represented as physical (electronic and/or magnetic) quantities within the registers and memories into other data similarly represented as physical quantities within memories or registers or other such information storage, transmission, processing, or display components.

Embodiments described herein may be discussed in the general context of processor-executable instructions residing on some form of non-transitory processor-readable medium, such as program modules or logic, executed by one or more computers, processors, or other devices. Generally, program modules include routines, programs, objects, components, data structures, etc., that perform particular tasks or implement particular abstract data types. The functionality of the program modules may be combined or distributed as desired in various embodiments.

In the figures, a single block may be described as performing a function or functions; however, in actual practice, the function or functions performed by that block may be performed in a single component or across multiple components, and/or may be performed using hardware, using software, or using a combination of hardware and software. To clearly illustrate this interchangeability of hardware and software, various illustrative components, blocks, modules, circuits, and steps have been described generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure. Also, the example electronic device(s) described herein may include components other than those shown, including well-known components.

The techniques described herein may be implemented in hardware, or a combination of hardware with firmware and/or software, unless specifically described as being implemented in a specific manner. Any features described as modules or components may also be implemented together in an integrated logic device or separately as discrete but interoperable logic devices. If implemented in software, the techniques may be realized at least in part by a non-transitory computer/processor-readable storage medium comprising computer/processor-readable instructions that, when executed, cause a processor and/or other components of a computer or electronic device to perform one or more of the methods described herein. The non-transitory processor-readable data storage medium may form part of a computer program product, which may include packaging materials.

The non-transitory processor-readable storage medium (also referred to as a non-transitory computer-readable storage medium) may comprise random access memory (RAM) such as synchronous dynamic random access memory (SDRAM), read only memory (ROM), non-volatile random access memory (NVRAM), electrically erasable programmable read-only memory (EEPROM), FLASH memory, other known storage media, and the like. The techniques additionally, or alternatively, may be realized at least in part by a processor-readable communication medium that carries or communicates code in the form of instructions or data structures and that can be accessed, read, and/or executed by a computer or other processor.

The various illustrative logical blocks, modules, circuits and instructions described in connection with the embodiments disclosed herein may be executed by one or more processors, such as host processor(s) or core(s) thereof, digital signal processors (DSPs), general purpose microprocessors, application specific integrated circuits (ASICs), application specific instruction set processors (ASIPs), field programmable gate arrays (FPGAs), sensor processors, microcontrollers, or other equivalent integrated or discrete logic circuitry. The term "processor" or the term "controller" as used herein may refer to any of the foregoing structures, any other structure suitable for implementation of the techniques described herein, or a combination of such structures. In addition, in some aspects, the functionality described herein may be provided within dedicated software modules or hardware modules configured as described herein. Also, the techniques could be fully implemented in one or more circuits or logic elements. A general purpose processor may be a microprocessor, but in the alternative, the processor may be any conventional processor, controller, microcontroller, or state machine. A processor may also be implemented as a combination of computing devices, e.g., a plurality of microprocessors, one or more microprocessors in conjunction with an ASIC or DSP, or any other such configuration or suitable combination of processors.

In various example embodiments discussed herein, a chip is defined to include at least one substrate typically formed from a semiconductor material. A single chip may for example be formed from multiple substrates, where the substrates are mechanically bonded to preserve the functionality. Multiple chip (or multi-chip) includes at least two substrates, wherein the two substrates are electrically connected, but do not require mechanical bonding.

A package provides electrical connection between the bond pads on the chip (or for example a multi-chip module) to a metal lead that can be soldered to a printed circuit board (or PCB). A package typically comprises a substrate and a cover. An Integrated Circuit (IC) substrate may refer to a silicon substrate with electrical circuits, typically CMOS circuits but others are possible and anticipated. A MEMS substrate provides mechanical support for the MEMS structure(s). The MEMS structural layer is attached to the MEMS substrate. The MEMS substrate is also referred to as handle substrate or handle wafer. In some embodiments, the handle substrate serves as a cap to the MEMS structure.

Some embodiments may, for example, comprise an ultrasonic transducer device. This ultrasonic transducer device may operate in any suitable ultrasonic range. In some embodiments, the ultrasonic transducer device may be or include a split-electrode ultrasonic transducer which may be an air coupled PMUT. In some embodiments, the ultrasonic transducer device may include a digital signal processor (DSP) or other controller or processor which may be disposed as a part of an ASIC which may be integrated into the same package as the split-electrode ultrasonic transducer.

Example Device

Figure 1B:
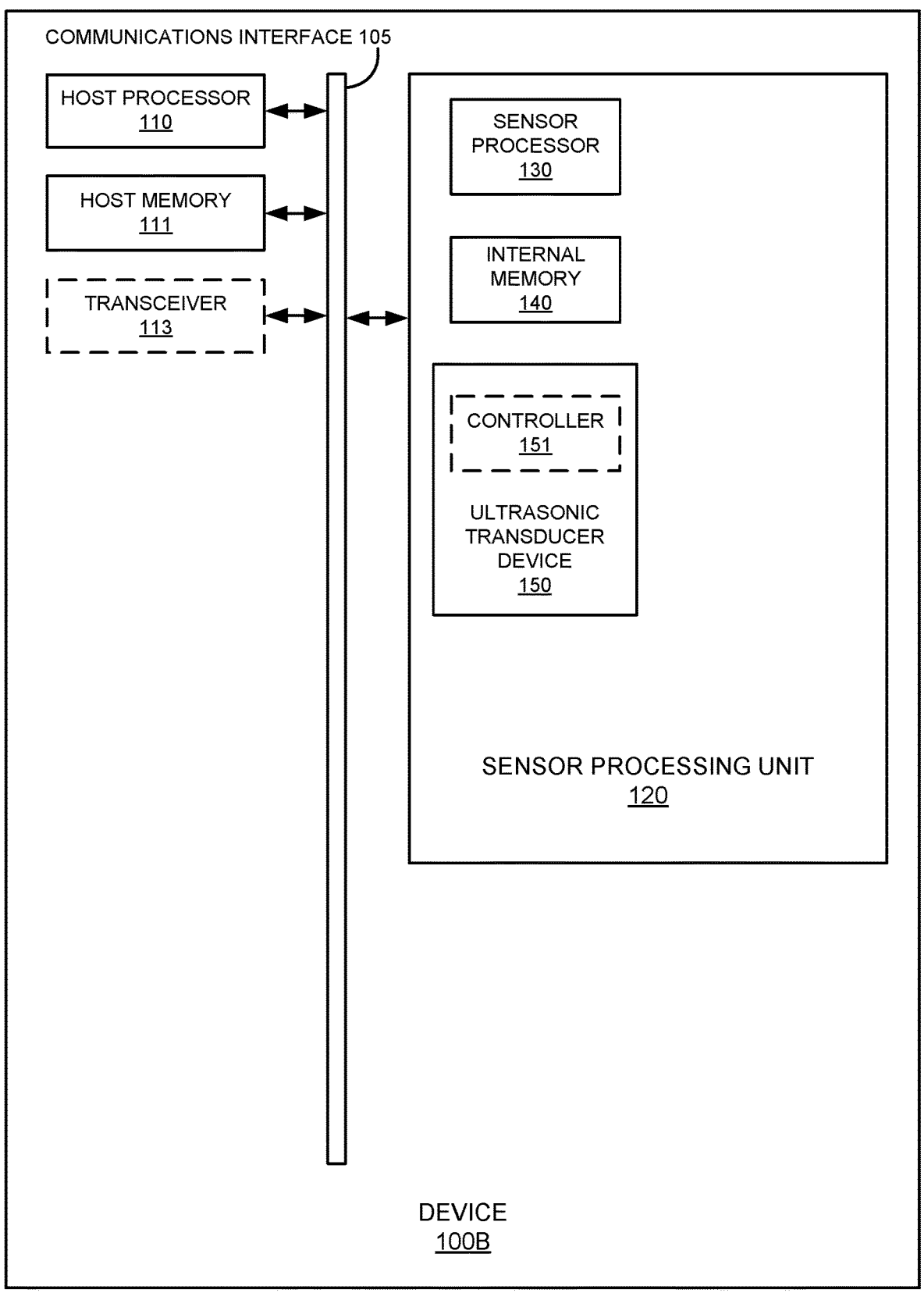

FIGS. 1A and 1B show some example components of a device 100 which utilizes an ultrasonic transducer device 150, according to various embodiments. Some examples of a device 100 may include, but are not limited to: remote controlled vehicles, virtual reality remotes, a telepresence robot, an electric scooter, an electric wheelchair, a wheeled delivery robot, a flying drone operating near a surface or about to land on or take off from a surface, a wheeled delivery vehicle, an automobile, an autonomous mobile device, a floor vacuum, a smart phone, a tablet computer, and a robotic cleaning appliance. By way of example, and not of limitation, the device 100 may utilize one or more ultrasonic transducer devices 150 to track the location of the device 100 in space, to detect the presence of objects in the environment of the device 100, to sense the absences of objects in the environment of device 100, to characterize objects sensed in the environment of device 100, and/or to avoid objects in the environment of the device 100.

FIG. 1A shows a block diagram of components of an example device 100A, in accordance with various aspects of the present disclosure. As shown, example device 100A comprises a communications interface 105, a host processor 110, host memory 111, and at least one ultrasonic transducer device 150. In some embodiments, device 100 may additionally include one or more of a transceiver 113, and one or more motion sensors or other types of sensors. Some embodiments may include sensors used to detect motion, position, or environmental context; some examples of these sensors may include, but are not limited to, infrared sensors, cameras, microphones, and global navigation satellite system sensors (i.e., a global positioning system receiver). As depicted in FIG. 1A, included components are communicatively coupled with one another, such as, via communications interface 105.

The host processor 110 may, for example, be configured to perform the various computations and operations involved with the general function of device 100. Host processor 110 can be one or more microprocessors, central processing units (CPUs), DSPs, general purpose microprocessors, ASICs, ASIPs, FPGAs or other processors which run software programs or applications, which may be stored in host memory 111, associated with the general and conventional functions and capabilities of device 100.

Communications interface 105 may be any suitable bus or interface, such as a peripheral component interconnect express (PCIe) bus, a universal serial bus (USB), a universal asynchronous receiver/transmitter (UART) serial bus, a suitable advanced microcontroller bus architecture (AMBA) interface, an Inter-Integrated Circuit (I2C) bus, a serial digital input output (SDIO) bus, or other equivalent and may include a plurality of communications interfaces. Communications interface 105 may facilitate communication between SPU 120 and one or more of host processor 110, host memory 111, transceiver 113, ultrasonic transducer device 150, and/or other included components.

Host memory 111 may comprise programs, modules, applications, or other data for use by host processor 110. In some embodiments, host memory 111 may also hold information that that is received from or provided to sensor processing unit 120 (see e.g., FIG. 1B). Host memory 111 can be any suitable type of memory, including but not limited to electronic memory (e.g., read only memory (ROM), random access memory (RAM), or other electronic memory).

Transceiver 113, when included, may be one or more of a wired or wireless transceiver which facilitates receipt of data at device 100 from an external transmission source and transmission of data from device 100 to an external recipient. By way of example, and not of limitation, in various embodiments, transceiver 113 comprises one or more of: a cellular transceiver, a wireless local area network transceiver (e.g., a transceiver compliant with one or more Institute of Electrical and Electronics Engineers (IEEE) 802.11 specifications for wireless local area network communication), a wireless personal area network transceiver (e.g., a transceiver compliant with one or more IEEE 802.15 specifications (or the like) for wireless personal area network communication), and a wired a serial transceiver (e.g., a universal serial bus for wired communication).

Ultrasonic transducer device 150 includes a split-electrode ultrasonic transducer of the type described herein and is configured to emit and receive ultrasonic signals. In some embodiments, ultrasonic transducer device 150 may include a controller 151 for controlling the operation of the split-electrode ultrasonic transducer and/or other components of ultrasonic transducer device 150. The controller 151 may be any suitable controller, many types of which have been described here. For example, controller 151 may turn amplifiers on or off, turn transmitters on or off, and/or operate selectable switches to electrically couple certain segments of electrodes during transmitting or during receiving and/or couple segments of electrodes to a drive transmitter, to ground, and/or to a front-end amplifier. Controller 151 may enable different modes of operation (e.g., transmitting, receiving, or continuous operation) and may enable variations within a mode (e.g., transmitting with some electrodes, but not others; and/or receiving with some electrodes, but not others). Additionally, or alternatively, in some embodiments, one or more aspects of the operation of ultrasonic transducer device 150 or components thereof may be controlled by an external component such as sensor processor 130 and/or host processor 110.

FIG. 1B shows a block diagram of components of an example device 100B, in accordance with various aspects of the present disclosure. Device 100B is similar to device 100A except that it includes a sensor processing unit (SPU) 120 in which ultrasonic transducer device 150 is disposed. SPU 120, when included, comprises: a sensor processor 130; an internal memory 140; and at least one ultrasonic transducer device 150. In some embodiments, SPU 120 may additionally include one or more motion sensors and/or one or more other sensors such a light sensor, infrared sensor, GNSS sensor, microphone, etc. In various embodiments, SPU 120 or a portion thereof, such as sensor processor 130, is communicatively coupled with host processor 110, host memory 111, and other components of device 100 through communications interface 105 or other well-known means. SPU 120 may also comprise one or more communications interfaces (not shown) similar to communications interface 105 and used for communications among one or more components within SPU 120.

Sensor processor 130 can be one or more microprocessors, CPUs, DSPs, general purpose microprocessors, ASICs, ASIPs, FPGAs or other processors that run software programs, which may be stored in memory such as internal memory 140 (or elsewhere), associated with the functions of SPU 120. In some embodiments, one or more of the functions described as being performed by sensor processor 130 may be shared with or performed in whole or in part by another processor of a device 100, such as host processor 110.

Internal memory 140 can be any suitable type of memory, including but not limited to electronic memory (e.g., read only memory (ROM), random access memory (RAM), or other electronic memory). Internal memory 140 may store algorithms, routines, or other instructions for instructing sensor processor 130 on the processing of data output by one or more of ultrasonic transducer device 150 and/or other sensors. In some embodiments, internal memory 140 may store one or more modules which may be algorithms that execute on sensor processor 130 to perform a specific function. Some examples of modules may include, but are not limited to: statistical processing modules, motion processing modules, object detection modules, and/or decision-making modules.

Ultrasonic transducer device 150, as previously described, includes a split-electrode ultrasonic transducer of the type described herein and is configured to emit and receive ultrasonic signals. In some embodiments, ultrasonic transducer device 150 may include a controller 151 for controlling the operation of the split-electrode ultrasonic transducer and/or other components of ultrasonic transducer device 150. The controller 151 may be any suitable controller, many types of which have been described here. For example, controller 151 may operate selectable switches to electrically couple certain segments of electrodes during transmitting or during receiving and or couple segments of electrodes to a drive transmitter, to ground, and/or to a front-end amplifier. Additionally, or alternatively, in some embodiments, one or more aspects of the operation of electrode ultrasonic transducer device 150 or components thereof may be controlled by an external component such as sensor processor 130 and/or host processor 110. Ultrasonic transducer device 150 is communicatively coupled with sensor processor 130 by a communications interface, bus, or other well-known communication means.

Example Split-Electrode Piezoelectric Transducer

Figure 2A:
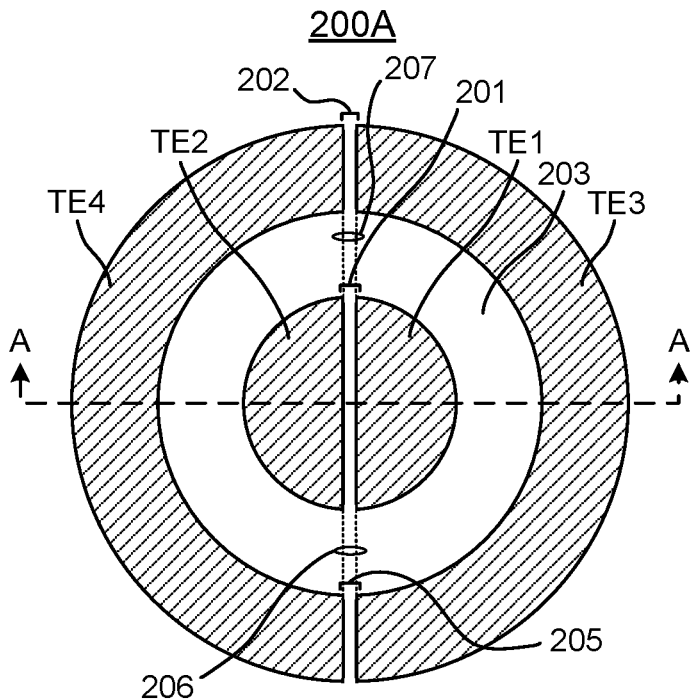
FIG. 2A shows a top plan view of a split-electrode transducer, in accordance with various embodiments.

FIG. 2A shows a top plan view of a split-electrode transducer 200A, in accordance with various embodiments. In some embodiments, split-electrode piezoelectric transducer 200A is an ultrasonic transducer and operates in the ultrasonic range. In some embodiments, split-electrode transducer 200A is a Piezoelectric Micromachined Ultrasonic Transducer (PMUT), which may be an air-coupled PMUT. In some air coupled ultrasonic transducer embodiments, for example, split-electrode piezoelectric transducer 200A operates in the 60 to 200 kHz range. In some air coupled ultrasonic transducer embodiments, for example, split-electrode piezoelectric transducer 200A operates in the 40 to 400 kHz range; where higher frequencies may be used for sensing objects that are very near to a transducer. In other embodiments of an ultrasonic transducer which is not air coupled (i.e., the transducer is coupled to other media such as liquids, human flesh, or solids), different operating frequency ranges are possible. In a first example, in some medical device embodiments such as for ultrasound probes, an ultrasonic transducer as described herein may operate in the 1-10 MHz range. In a second example, in some fingerprint sensing embodiments, an ultrasonic transducer as described herein may operate in the 10-60 MHz range. Section line A-A shows the position and direction of a side sectional view illustrated in FIG. 2B.

With reference to FIG. 2A, the top view illustrates that transducer 200A is formed in a circular shape, however other shapes may be utilized. Some non-limiting examples of other shapes include: square, rectangular, hexagonal, and ellipse.

Figure 2B:
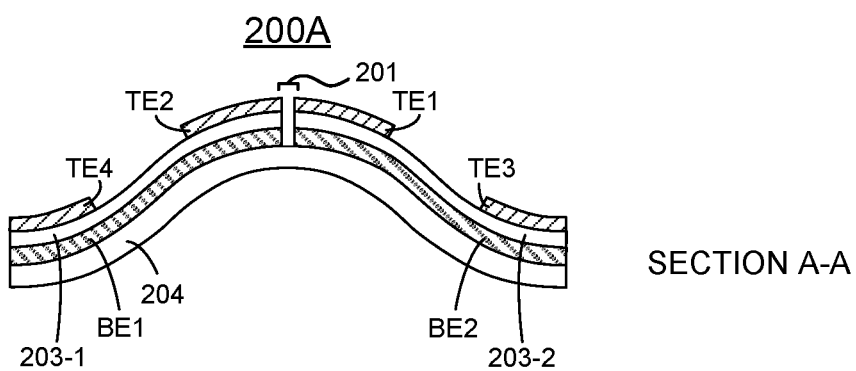
FIG. 2B shows a sectional side elevational view of the split-electrode transducer of FIG. 2A, in accordance with various embodiments.

FIG. 2B shows a sectional side elevational view A-A of the split-electrode transducer 200A of FIG. 2A, in accordance with various embodiments.

Figure 7A:
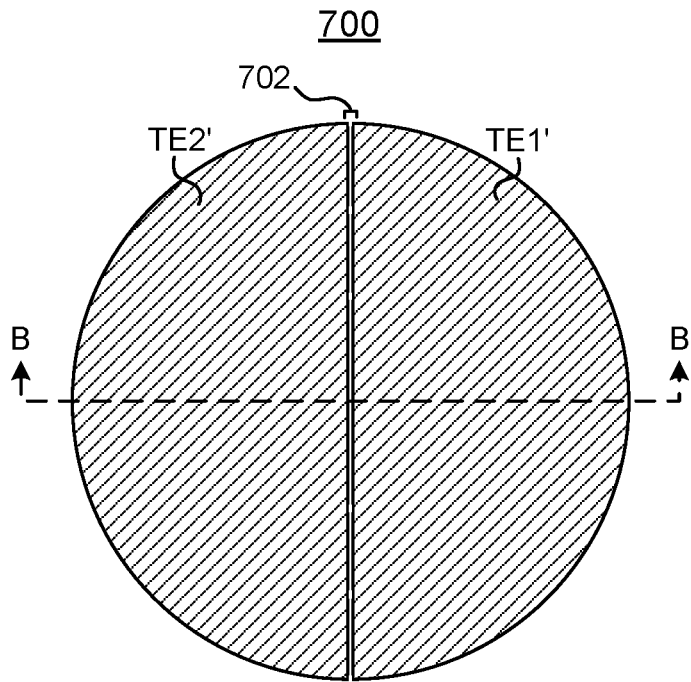
FIG. 7A shows a top plan view of a split-electrode transducer, in accordance with various embodiments.
Figure 7B:
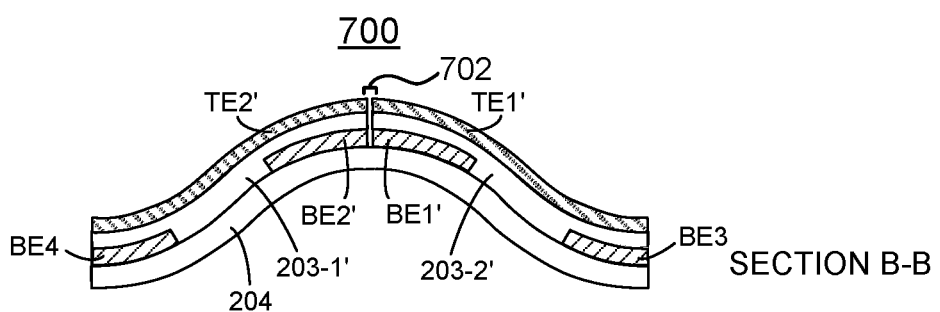
FIG. 7B shows a sectional side elevational view B-B of the split-electrode transducer of FIG. 7A, in accordance with various embodiments.

With reference to FIGS. 2A and 2B, split-electrode piezoelectric transducer 200A includes: a top electrode layer, TE; a bottom electrode layer, BE; a membrane layer 204, and a piezoelectric layer 203. As will be described, the depicted order of the layers is just one example of their ordering; other orders of these layers may be utilized in some embodiments so long as the piezoelectric material is disposed between the TE layer and the BE layer. For example, an alternative ordering of the layers is illustrated in FIGS. 7A and 7B. In some embodiments, other layers such as protective layers, filler layers, and/or electrically insulating layers may be included. These other layers have not been depicted in order to improve clarity. It should be appreciated that membrane 204 moves up and down (relative to FIG. 2B) at a desired frequency to produce sound through the displacement of membrane 204, and that in FIG. 2B membrane 204 is depicted in a "displaced up" position of the transducer.

With continued reference to FIG. 2A, the BE layer comprises conductive material disposed above and coupled with the membrane layer 204 and is split into at least two portions depicted as a first bottom electrode BE1, and a second bottom electrode BE2. In some embodiments, the first bottom electrode BE1 and the second bottom electrode BE2 are substantially equal in surface area.

It should be appreciated that electrical traces are required to be coupled to the electrodes in order to route various signals and/or provide various couplings (such as to another electrode, to ground, etc.), however in the interest of clarity these traces are not illustrated. Any suitable routing may be used for such these traces.

With continued reference to FIGS. 2A and 2B, a piezoelectric layer 203 is disposed above and coupled with the bottom electrode layer (i.e., bottom electrodes BE1 and BE2). In some embodiments, the piezoelectric layer 203 may comprise a first piezoelectric portion 203-1 disposed above the first bottom electrode BE1 and a second piezoelectric portion 203-2 disposed above the second bottom electrode BE2. In the embodiment of FIG. 2B, the gap represented by dashed lines 206 and 207 in FIG. 2A is etched or otherwise created to form two segments of the piezoelectric layer 203. In some embodiments, the surface area (i.e., surface area from a top plan view measurement of surface area) of first piezoelectric portion 203-1 and second piezoelectric portion 203-2 may be equal or substantially equal (e.g., within manufacturing tolerances of e.g., a few percent) to one another. In other embodiments, where the top electrode layer TE and the bottom electrode layer BE may be etched while the piezoelectric layer 203 is not. In such an embodiment, piezoelectric layer 203 may be a single, unetched layer that is not divided into multiple parts and the gap in piezoelectric layer 203 represented by dashed lines 206 and 207 in FIG. 2A would not be present.

With continued reference to FIGS. 2A and 2B, a top electrode layer TE comprised of conductive material is disposed above and coupled with the piezoelectric layer 203. Top electrode layer TE comprises a segmented center electrode with segments TE1 and TE2 that are disposed above a center portion of the membrane layer 204. Gap 201, illustrated in FIG. 2A, shows the location of an electrical disconnect/gap between center electrode segments TE1 and TE2. The top electrode layer TE also comprises a segmented outer electrode with segments TE3 and TE4 that are spaced apart, outward, from the segmented center electrode segments TE1 and TE2. In a circular embodiment, as depicted in FIG. 2A, the outer electrode segments TE3 and TE4 are spaced radially outward, apart from the center electrode segments TE1 and TE2. Gaps 202 and 205, illustrated in FIG. 2A, show the locations of electrical disconnects/gaps between outer electrode segments TE3 and TE4. The segmented outer electrode (e.g., segments TE3 and TE4) is disposed such that it is spaced apart, away from the center of the membrane layer and around (i.e., surrounding except for the gaps) the segmented center electrode (e.g., around segments TE1 and TE2). In FIG. 2A, outer electrode segments TE3 and TE4 form a segmented circular ring around segments TE1 and TE2 of a circular center. However, in other transducer shapes (e.g., square, hexagonal, rectangular, oval) the segmented outer electrode as well as the center electrodes may have other shapes (e.g., square, hexagonal, rectangular, oval) and the segmented outer electrode forms a perimeter or periphery which is spaced apart and outward from the segmented center electrodes. Although the center electrode and outer electrode are each divided into two segments, following the same principles each may be divided into a larger number of segments. For example, each of the center electrode and the outer electrode may be divided into three segments, four segments, five segments six segments, etc. In some embodiments, each of the segments of the center electrode is equal or substantially equal (e.g., within manufacturing tolerances of a few percent) in surface area to one another. In some embodiments, each of the segments of the outer electrode is equal or substantially equal (e.g., within manufacturing tolerances of a few percent) in surface area to one another. In some embodiments, each of the individual segments of the segmented center electrode and of the segmented outer electrode is equal or substantially equal (e.g., within manufacturing tolerances of a few percent) in surface area to one another. That is, in some embodiments the plan view surface area of TE1=the surface area of TE2=the surface area of TE3=the surface area TE4. It should be appreciated that the gaps 202 and 205 between the outer electrode segments TE3 and TE4 are not required to be aligned with the gap 201 between the center electrode segments TE1 and TE2. They may be offset by any suitable angle, such as 7 degrees, 20 degrees, 37 degrees, 45 degrees, 90 degrees, etc.

Figure 2C:
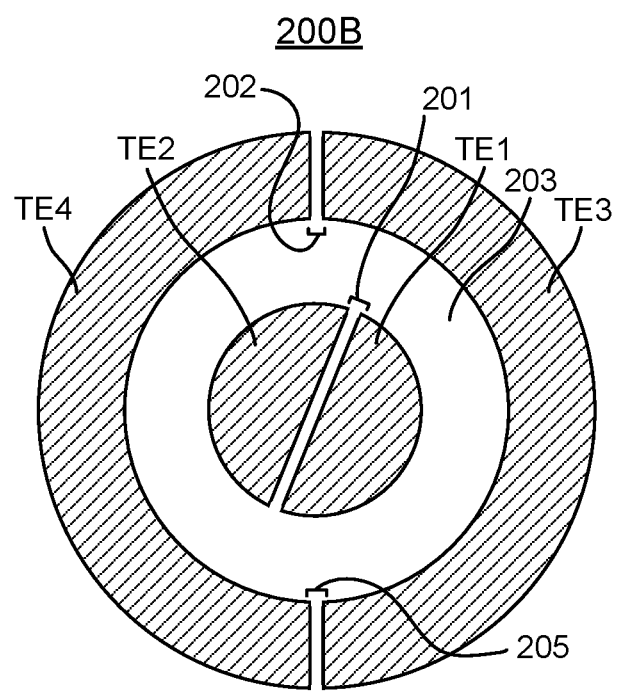
FIG. 2C shows a top plan view of a split-electrode transducer, in accordance with various embodiments.

With reference to FIG. 2C, a top view is illustrated of an example split-electrode transducer 200B, in accordance with various embodiments. FIG. 2C shows a circular embodiment of a split-electrode transducer where the gaps (202, 205) between the outer electrode segments TE3 and TE4 are not aligned with the gap 201 between the center electrode segments TE1 and TE2. In some such embodiments, the lack of alignment between the gap 201 and gaps 202 and 205 reduces physical weakness of transducer 200B, and in particular the top electrode layer TE, by positioning gaps along different axes instead of all being positioned along the same axis. As described above in conjunction with FIG. 2A, in other transducer shapes (e.g., square, hexagonal, rectangular, oval) the segmented outer electrode as well as the center electrodes may have other shapes (e.g., square, hexagonal, rectangular, oval). Electrical operation of the split-electrode transducer 200B is not altered, with respect to split electrode transducer 200A, when gap 201 is not aligned with gaps 202 and 205.

With continued reference to FIGS. 2A and 2B, a first segment TE4 of the segmented outer electrode and a first segment TE2 of the segmented center electrode are disposed above the first bottom electrode BEL while a second segment TE3 of the segmented outer electrode and a second segment TE1 of the segmented center electrode are disposed above the second bottom electrode B2. In some embodiments the segments TE1 and TE2 of the segmented center electrode and segments TE3 and TE4 of the segmented outer electrode are positioned on the piezoelectric layer 203 based on a curvature of the piezoelectric layer 203 when it is displaced up or down (shown displaced up in FIG. 2B). That is, they are arranged such that the curvature of the center electrode segments TE1 and TE2 is opposite of the curvature of the outer electrode segment TE3 and TE4 when transducer 200A is fully displaced up or fully displaced down. That is, one of the split center electrode and the split outer electrode inside the deflection point of the displaced piezoelectric layer 203 while the other is outside of a deflection point of the displaced piezoelectric layer 203.

With continued reference to FIGS. 2A and 2B, one way to mathematically describe the shapes of the top electrode layer (TE1, TE2, TE3, TE4) with respect to the piezoelectric layer 203 is that the top electrode layer is disposed above and coupled with the piezoelectric layer 203 and comprises a segmented first electrode (segmented center electrode segments TE1 and TE2) disposed above a section of the membrane layer 204, in which the Laplacian of the out-of-plane displacement in the piezoelectric layer 203 has a positive sign in a given displaced shape, and a segmented second electrode (segmented outer electrode segments TE3 and TE4) spaced radially apart from the segmented first electrode (TE1, TE2), in which the Laplacian of the out-of-plane displacement in the piezoelectric layer 203 has a negative sign in the same given displaced shape. Another way to mathematically describe the shapes of the top electrode layer (TE1, TE2, TE3, TE4) with respect to the piezoelectric layer 203 is that the top electrode layer is disposed above and coupled with the piezoelectric layer 203 and comprises a segmented first electrode (segmented center electrode segments TE1 and TE2) disposed above a section of the membrane layer 204, in which the sum of the normal components of the in-plane strain in the piezoelectric layer 203 has a positive sign in a given displaced shape, and a segmented second electrode (segmented outer electrode segments TE3 and TE4) spaced apart (radially apart in the depicted embodiment) from the segmented first electrode (TE1, TE2), in which the sum of the normal components of the in-plane strain in the piezoelectric layer 203 has a negative sign in the same given displaced shape.

With reference to FIG. 2B, split-electrode transducer 200A is shown with a curvature which occurs as the transducer 200A moves during operation. As depicted, in some instances during upward deflection of the piezoelectric layer 203, when segments TE1 and TE2 of the segmented center electrode (TE1 and TE2 together) present a concave surface disposed toward membrane layer 204; at the same time segments TE3 and TE4 of the segmented outer electrode (TE3 and TE4 together) present a convex surface oriented toward membrane layer 204. Similarly, in other instances during downward deflection of the piezoelectric layer 203 (not depicted), when segments TE1 and TE2 of the segmented center electrode (TE1 and TE2 together) present a convex surface disposed toward membrane layer 204; at the same time segments TE3 and TE4 of the segmented outer electrode (TE3 and TE4 together) present a concave surface oriented toward membrane layer 204. These concave and convex curvatures and orientations are due to the shape of the deflected piezoelectric layer 203 as it moves in response to an applied signal.

With reference to FIGS. 2A, 2B, and 2C, the depicted gaps may be air gaps or may be filled, such as with an insulative material. The width of the gaps is very small and may only be a few microns, in some embodiments. Generally, a gap is made as narrow as is feasible, as making it wider limits surface area of the split electrodes and reduces performance of the transducer. The lower limit of the narrowness of the gap widths is typically governed either by the limits of the lithography or other techniques used to deposit materials or etch the gaps or by the avoidance of fringe capacitive coupling between the electrodes on each side of the gap which may occur if the gap is too narrow. In some embodiments, conductive routing traces may be disposed in/routed through a gap. For example, the split center electrodes TE1 and TE2 may have one or more conductive routing traces which are disposed in gap 201. Accordingly, in such an embodiment, gap 201 may be wider than the minimum narrowness possible to facilitate presence of the conductive trace(s).

With reference to FIG. 2B, in some embodiments, an additional electrode (not depicted) can be added below membrane 204. In such embodiments, the additional electrode can be grounded and/or electrically isolated from bottom electrode layer BE and used as a shield to reduce interference.

Although described herein as an ultrasonic transducer, the principles of the split-electrode piezoelectric transducer 200 illustrated in FIGS. 2A, 2B, and 2C may be utilized with transducers operating in other frequency ranges (e.g., human audible or infrasound). Further, the principles may be applied to sonic transmitters or sonic receivers, not just to sonic transducers. For example, the principles described herein may be utilized to improve the receive function of a microphone.

Operation of the Example Split Electrode PMUT

Figure 3:
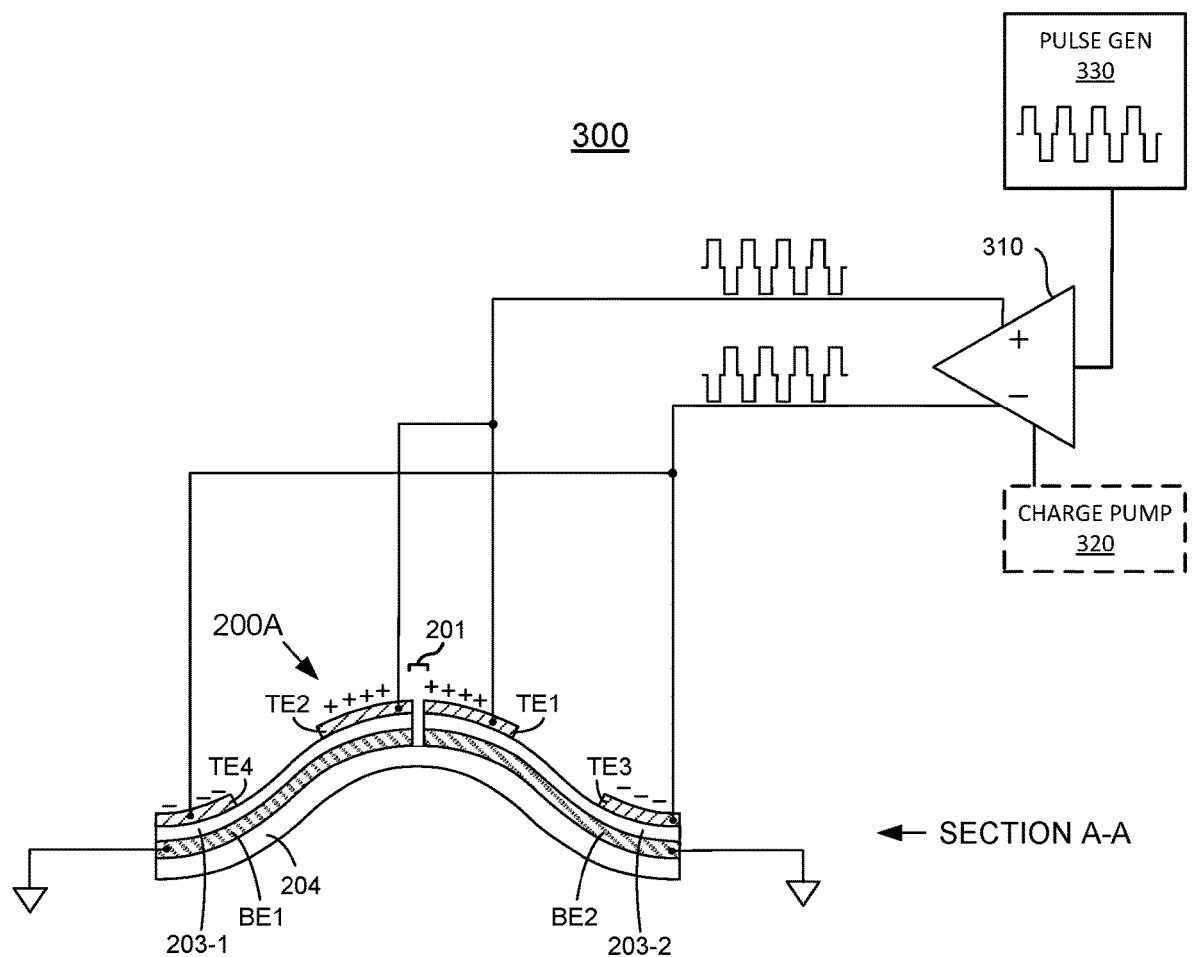
FIG. 3 illustrates operation of the split-electrode piezoelectric transducer of FIGS. 2A and 2B in a transmit mode, in accordance with various embodiments.

FIG. 3 illustrates operation of the split-electrode PMUT 200A of FIGS. 2A and 2B in a transmit (Tx) mode, in accordance with various embodiments. In FIG. 3, a circuit 300 is depicted which includes split-electrode PMUT 200A. As illustrated, a signal/pulse generator 330 is coupled with the input of a drive transmitter 310 generates and provides a repeating pulse or repeating waveform on the input. In some embodiments, a charge pump 320 may also be coupled with drive transmitter 310. Charge pump 320, when included, supplies additional charge for drive transmitter 310 to amplify the input to drive transmitter 310. In some embodiments, for example, a charge pump may be included when aluminum nitride (AlN) is used in the piezoelectric layer 203 as certain configurations of such a split-electrode transducer may require additional supplied charge (voltage), over the voltage natively provided by drive transmitter 310, to transmit.

In the Tx mode illustrated in FIG. 3, in some differential drive embodiments, center electrode segment TE1 and center electrode segment TE2 are connected together (as a unified center electrode TE1,TE2), while outer electrode segment TE3 and outer electrode segment TE4 are connected together (as a unified outer electrode TE3,TE4). A differential drive signal from the non-inverted output of drive transmitter 310 is applied on center electrode TE1, TE2; and from the inverted output of drive transmitter 310 the 180 degree out of phase version of the drive signal is applied on outer electrode TE34. BE1 and BE2 are both grounded. By driving differential signals simultaneously on both the center electrode TE1, TE2 and the outer electrode TE3, TE4, the achieved displacement of the split electrode PMUT 200A is increased compared to driving only on the either the center electrode TE1, TE2 or on outer electrode TE3, TE4. The increased displacement results in increased transmission range of the transmitted ultrasonic signal over conventional approaches.

Transmit modes that do not utilize differential drive may be employed, in some embodiments. For example, in a continuous mode of operation (rather than where driving is pulsed on/off), transmitting may be accomplished by driving only the segmented center electrodes TE1, TE2 (at the same time with the same signal) but not driving the segmented outer electrodes TE3, TE4; or transmitting may be accomplished by driving only the segmented outer electrodes TE3, TE4 (at the same time with the same signal) but not driving the segmented center electrodes TE1, TE2. In a continuous mode of operation, some TE electrodes may be driven while other TE electrodes are used to receive. For example, while a signal is driven on one or both segmented center electrodes TE1 and TE2, returned signals may be received on one or both of segmented outer electrodes TE3 and TE4. Controller 151 may configure components of an ultrasonic transducer device 150 to operate in a continuous mode or a differential mode.

To transmit with some modicum of amplitude control, instead of driving on all four of the TE electrodes, only one, two or three of the TE electrodes may be driven. To support a continuous mode of operation, undriven TE electrodes may be used to simultaneously receive while other TE electrodes are being driven. Controller 151 may configure components of an ultrasonic transducer device 150 to drive with selected electrodes and/or to receive with selected electrodes.

Figure 4A:
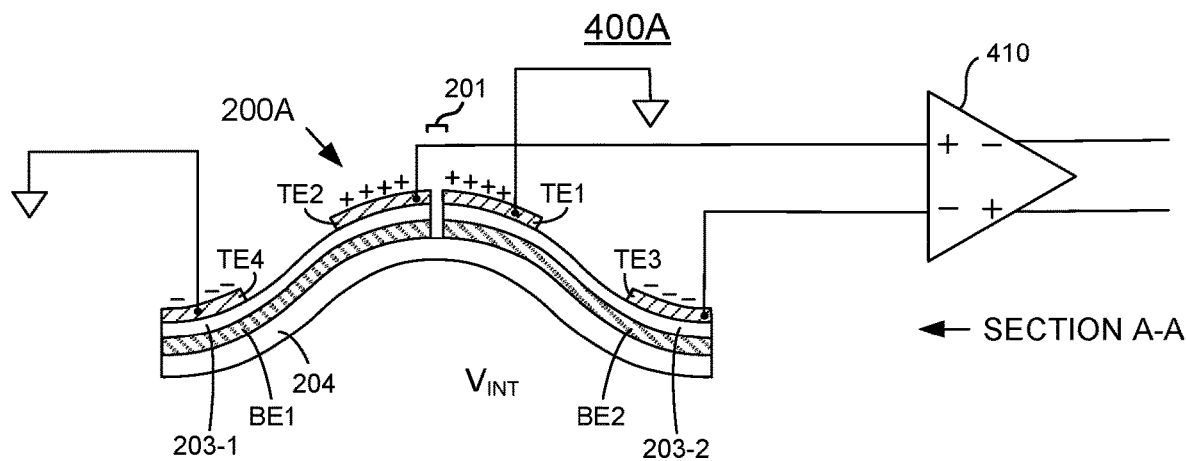
FIG. 4A illustrates operation of the split-electrode piezoelectric transducer of FIGS. 2A and 2B in a receive mode, in accordance with various embodiments.

FIG. 4A illustrates operation of the split-electrode PMUT 200A of FIGS. 2A and 2B in a receive mode, in accordance with various embodiments. In FIG. 4A, a circuit 400A is depicted which includes split-electrode PMUT 200A. In the Rx mode, BE1 and BE2 are floating and TE1 and TE4 are grounded. Center electrode segment TE2 and outer electrode segment TE3 are connected, respectively, to the two differential inputs of front-end amplifier 410 of the receive circuitry. As depicted, for example, split electrode segment TE2 is coupled with the non-inverting input, while outer electrode segment TE3 is coupled to the inverting input. In this setup, the path from ground through TE1 to BE2 to TE3 to the inverting input of front-end amplifier 410 represents a set of two stacked (i.e., series) capacitors, such that the overall capacitance in this path is halved, and the voltage is consequently doubled while doubling the source impedance. More particularly, the first capacitor has plates of TE1 and BE2 separated by a piezoelectric layer 203-2 as a dielectric, while the second capacitor has plates of BE2 and TE3 separated by piezoelectric layer 203-2 as a dielectric. Because BE2 is a common plate/node in this set of capacitors, it provides a series electrical coupling between these two capacitors. The same is true of the path from ground through TE4 to BE1 to TE2 to the non-inverting input of front-end amplifier 410, which represents a second set of two stacked (i.e., series) capacitors. More particularly, the first capacitor has plates of TE4 and BE1 separated by a piezoelectric layer 203-1 as a dielectric, while the second capacitor has plates of BE2 and TE2 separated by piezoelectric layer 203-1 as a dielectric. Because BE1 is a common plate/node in this second set of capacitors, it provides a series electrical coupling between these two capacitors. By using both TE2 and TE3 as differential input to the front end, the receive voltage is doubled again for an overall four times gain in comparison to a transducer which only utilizes a center electrode design. This four times gain increases the Rx sensitivity over conventional approaches.

Figure 4B:
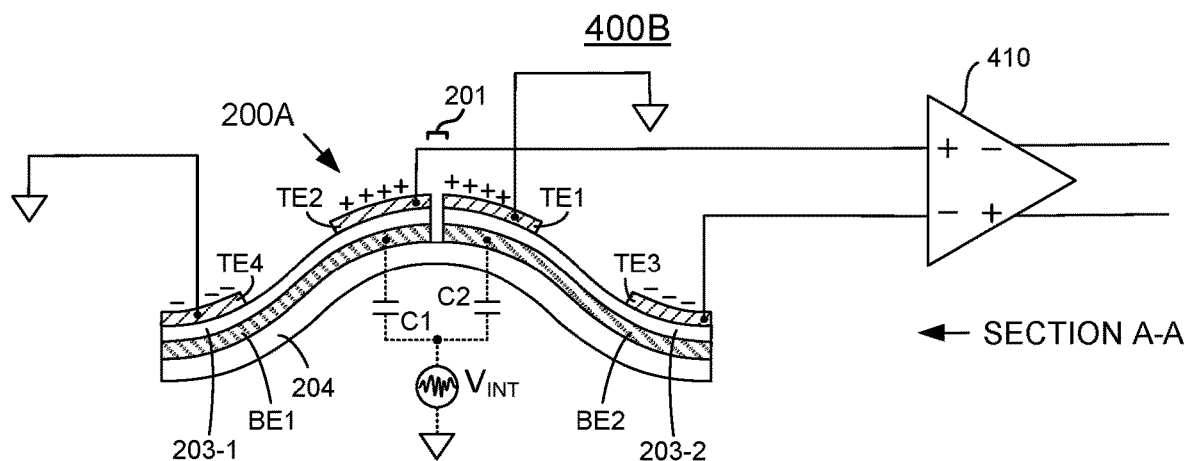
FIG. 4B illustrates operation of the split-electrode piezoelectric transducer of FIGS. 2A and 2B in a receive mode, in accordance with various embodiments.

FIG. 4B illustrates operation of the split-electrode piezoelectric transducer 200A of FIGS. 2A and 2B in a receive mode, in accordance with various embodiments. In FIG. 4B, a circuit 400B is depicted which includes split-electrode PMUT 200A. When the surface areas of TE1, TE2, TE3, and TE4, are equal or substantially equal, the effective capacitances of C1 and C2 are equal, and any interference signal ($V_{INT}$) becomes common mode and is reduced at the output of amplifier 410 by the common mode rejection ratio of amplifier 410.

Figure 5A:
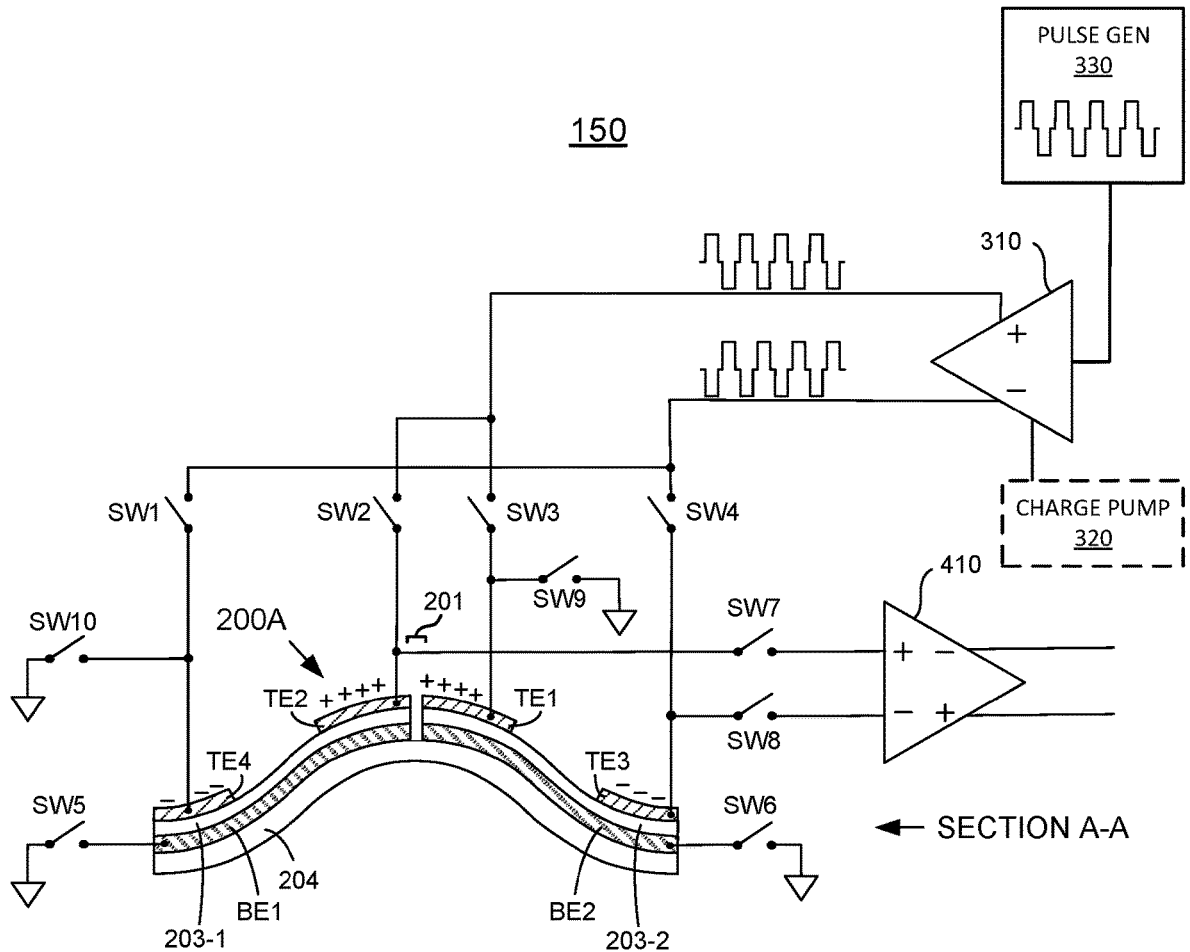
FIG. 5A illustrates an ultrasonic transducer device, in accordance with various embodiments.

FIG. 5A illustrates an ultrasonic transducer device 150, in accordance with various embodiments. FIG. 5A represents a combination of the circuits and as components illustrated in FIGS. 4A and 4B in order to form an ultrasonic transducer device 150 which is configured to both transmit and receive. Selectable switches SW1, SW2, SW3, SW4, SW5, SW6, SW7, SW8, SW9, and SW10 have also been added to select various modes of operation. These selectable switches are all shown in an open position. In some embodiments, controller 151 (not depicted) or another processor or logic operates the selectable switches to select different modes of operation. In some embodiments, SW1, SW2, SW3, and SW4 are high voltage switches and operate to pass high voltages during transmitting. In some embodiments, switches SW5 and SW6 are low voltage switches. In some embodiments, SW7, SW8, SW9, and SW10 are high voltage switches which provide a low Equivalent Series Resistance (ESR) and also block high voltages from front-end amplifier 410 when transmitting is occurring. In some embodiments, high voltage is in the range of 4V to ~120V or more. In some embodiments, high voltage is in the range of ~10V to ~40V. In some embodiments, low voltage is in the range of 1V to ~3.5V or slightly more (e.g., 5V). In some embodiments, low voltage is in the range of 1.2V to 2.2V or slightly more.

Figure 5B:
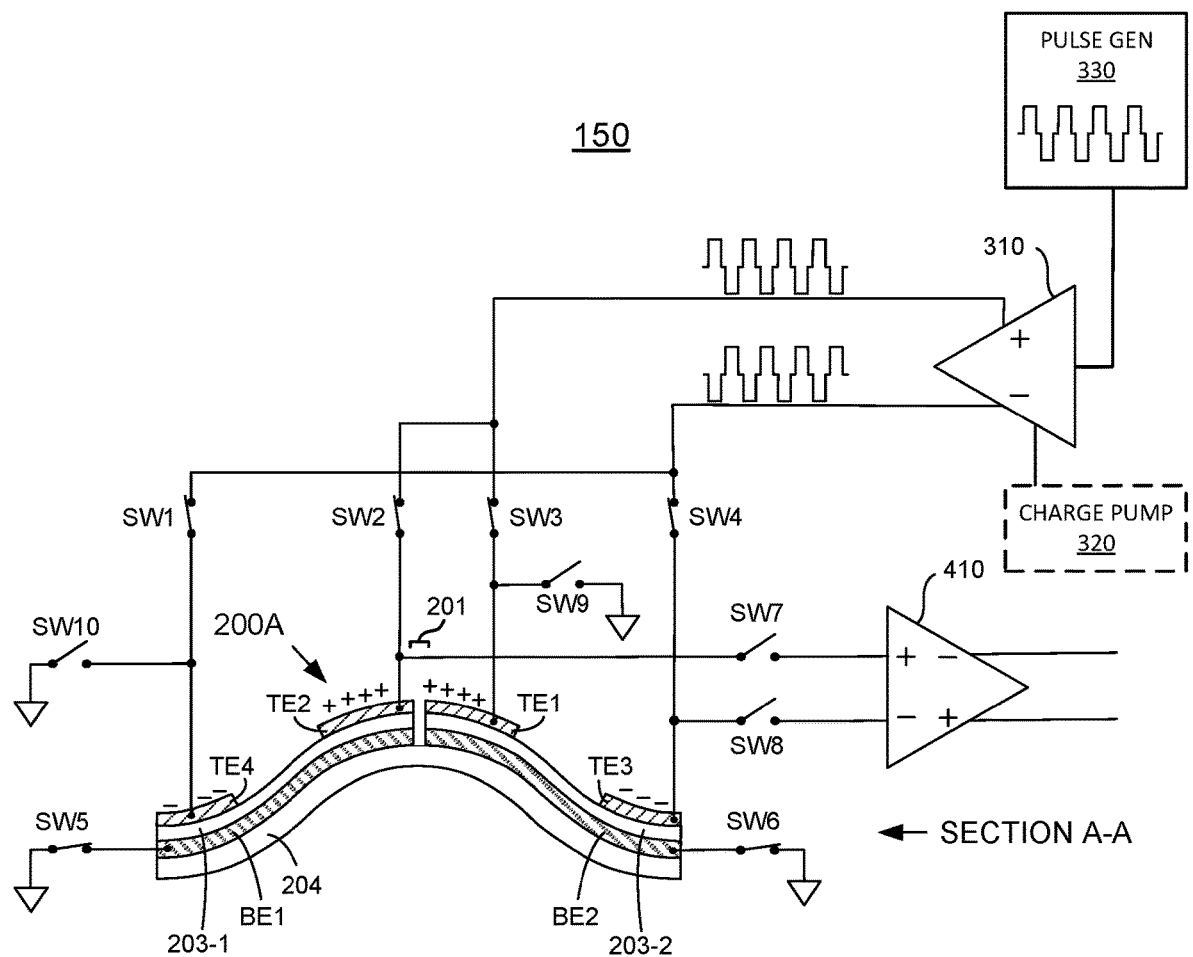
FIG. 5B illustrates the ultrasonic transducer device of FIG. 5A in a transmit configuration, in accordance with various embodiments.

FIG. 5B illustrates the ultrasonic transducer device 150 of FIG. 5A in a transmit configuration, in accordance with various embodiments. In such embodiments, controller 151 or another processor or logic, has closed selectable switches SW1, SW2, SW3, SW4, SW5 and SW6 and opened selectable switches SW7, SW8, SW9, and SW10 in response to an instruction to place PMUT 200A in a transmit mode. This creates the same conditions previously discussed in conjunction with FIG. 3, where: BE1 and BE2 are coupled to ground; the non-inverting output of drive transmitter 310 is coupled with center electrode segments TE1 and TE2; and the inverting output of drive transmitter 310 is coupled with outer electrode segments TE3 and TE4.

It should be appreciated that switches S1, S2, S3, and S4 may not be present or used in some embodiments. That is, the modes described herein, may be implemented without these switches. For example, in such embodiments, two transmitter 310 may instead be used (rather than the single depicted transmitter 310). The positive output of the first transmitter 310 is connected to TE2 and the negative output of the first transmitter 310 is connected to TE4. The positive output of the second transmitter 310 is connected to TE1 and the negative output of the second transmitter 310 is connected to TE3. Each of the transmitters 310 is designed to have a high-impedance state wherein the internal switches in a transmitter 310 may be turned off by controller 151 when it is not active and especially when the circuit is configured in receive mode.

Figure 5C:
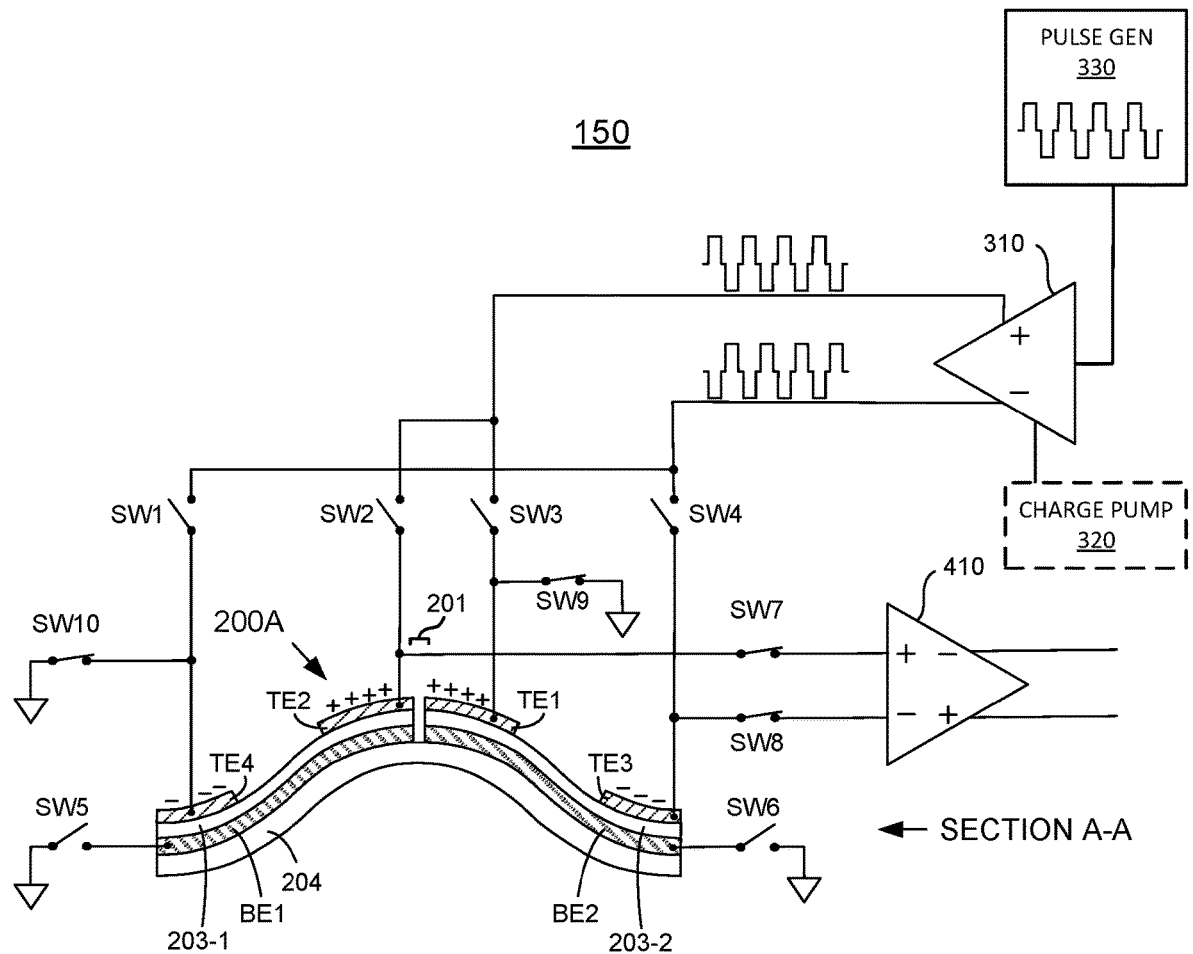
FIG. 5C illustrates the ultrasonic transducer device of FIG. 5A in a receive configuration, in accordance with various embodiments.

FIG. 5C illustrates the ultrasonic transducer device 150 of FIG. 5A in a receive configuration, in accordance with various embodiments. In such embodiments, controller 151 or another processor or logic, has opened selectable switches SW1, SW2, SW3, SW4, SW5 and SW6 and closed selectable switches SW7, SW8, SW9, and SW10 in response to an instruction to place PMUT 200A in a receive mode or an instruction to switch from a transmit mode to a receive mode. This creates the same conditions previously discussed in conjunction with FIG. 4A, where: BE1 and BE2 are floating and TE1 and TE4 are grounded. Center electrode segment TE2 and outer electrode segment TE3 are connected, respectively, to the two differential front-end inputs of the receive circuitry. In some embodiments, instead of immediately opening switches SW5 and SW6 when PMUT is switched from transmitting to receiving, controller 151 may leave them closed for a short period of time (such as the ringdown period after differential transmitting with transducer 200A, or slightly longer) in order to reduce the amplitude of membrane vibration caused by ringdown and thus control the gain (such as by preventing front-end amplifier 410 from being driven to saturation by a ringdown signal when it is set to amplify received signals that do not include much or any of the ringdown signal).

SW5 and SW6, when closed, reduce the signal received from the transducer 200A by shorting out the signal from TE1 and TE4. These switches can be opened and/or closed during a receive cycle. This can be used to reduce the overall dynamic range requirement of the front end and can be used to increase the gain (by opening these switches) during the receive cycle after a certain time has elapsed since the transmitting phase. In this manner front-end may be set at a higher gain, without clipping/saturation being caused by ringdown signals. In some embodiments, the ringdown period is at least as long as a transmit period immediately preceding the PMUT being switched from a transmit mode to a receive mode. Reducing the received signal by closing SW5 and SW6 may be utilized to create a "close object detection mode," which reduces the gain while sensing for nearby objects which would generate a strong return. In this manner, gain of the front-end amplifier 410 does not have to be adjusted to prevent saturation which might be caused by sensing nearby objects. Opening switches SW5 and SW6 allows switching from the close object detection mode to a "far object detection mode" due to increasing the gain. For example, if it is determined that there is no close object detected, switches SW6 and SW6 can be opened to detect for objects farther away.

When the capacitance of PMUT 200A (or 200B when it is utilized) is much larger than the parasitic capacitance (of front-end amplifier 410, wire bonds, etc.) any reduction in PMUT capacitance is beneficial. Thus, in this manner, the TE electrodes may be divided into more pieces than illustrated in order to increase the number of series capacitors and thus decrease capacitance. The gains realized from reducing the capacitance of the PMUT (via these further divisions of the top electrode (center and outer portions) and the bottom electrode) only diminishes when the PMUT capacitance becomes the same or less than the parasitic capacitance while in a receive mode. For example, the series stacking can be taken to the next level by splitting each top and bottom electrode up again. This would further increase the receive voltage. However, it would require connecting top electrode areas together without connecting the underlying bottom electrodes. In some embodiments, this connecting can be accomplished in a process where the bottom electrode is patterned before the deposition of the piezoelectric layer; or by connecting the top electrodes externally (e.g., with wire bonds or switches). The advantage of further stacking additional series capacitors disappears when the reduction in capacitance means that the PMUT capacitance becomes comparable to parasitic capacitance considering also that the latter might increase due to additional wire bonds, switches in the ASIC, etc.

Figure 5D:
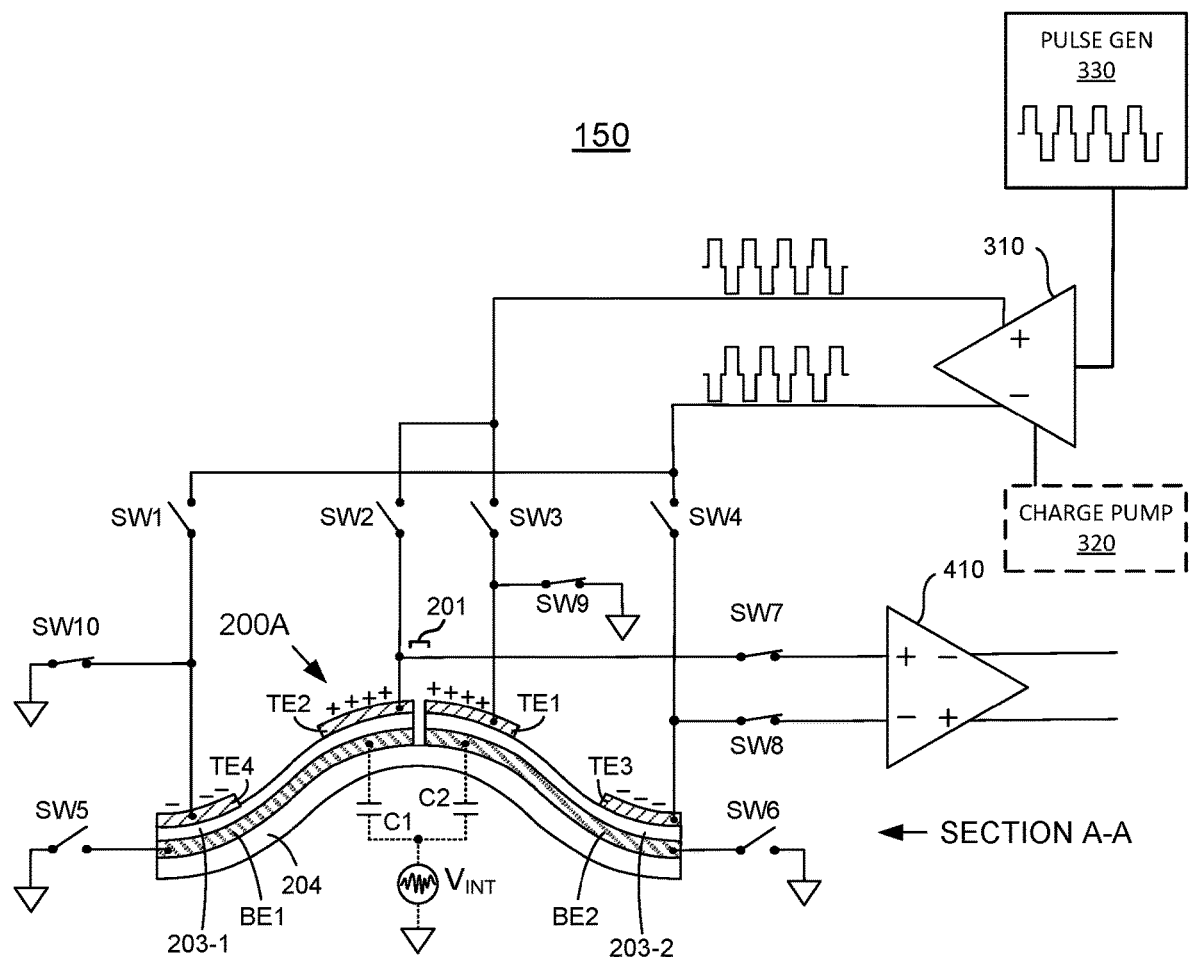
FIG. 5D illustrates the ultrasonic transducer device of FIG. 5A in a receive configuration, in accordance with various embodiments.

FIG. 5D illustrates the ultrasonic transducer device 150 of FIG. 5A in a receive configuration, in accordance with various embodiments. FIG. 5D is the same as FIG. 5C except that it illustrates an embodiments previously described in conjunction with FIG. 4B in which the surface areas of TE1, TE2, TE3, and TE4, are equal or substantially equal, causing the effective capacitances of C1 and C2 to be equal, and thus causing an interference signal ($V_{INT}$) to become common mode and rejected to ground.

Example Method of Manufacture

Figure 6:
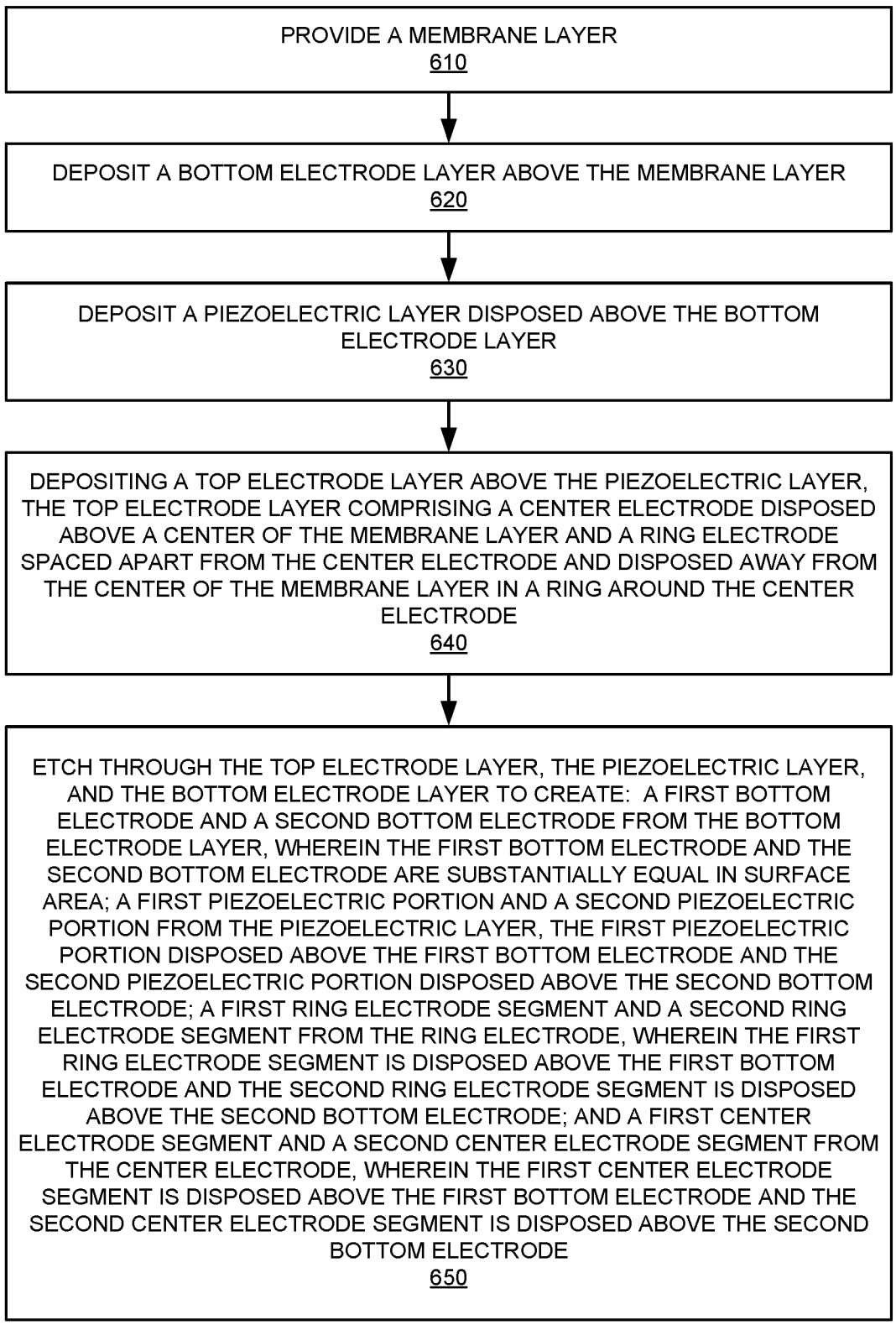
FIG. 6 illustrates a method of manufacture of a piezoelectric micromachined transducer, in accordance with various embodiments.

FIG. 6 illustrates a method of manufacture of a piezoelectric micromachined transducer, in accordance with various embodiments. In some embodiments, the piezoelectric micromachined transducer may operate in the ultrasonic range and it may be referred to as a PMUT. In some embodiments the piezoelectric micromachined transducer is air coupled. Procedures of the method illustrated by flow diagram 600 of FIG. 6 will be described with reference to elements and/or components of one or more of FIGS. 2A, 2B, and 2C. It is appreciated that in some embodiments, the procedures may be performed in a different order than described in a flow diagram, that some of the described procedures may not be performed, and/or that one or more additional procedures to those described may be performed.

With reference to FIG. 6, at procedure 610 of flow diagram 600, in various embodiments, a membrane layer is provided. In some embodiments, the membrane is provided or built-up through deposition, it can then be patterned as required to create gaps by using photolithographic patterning, etching, or lift-off. The membrane layer may be similar to membrane 204 of FIG. 2B.

With continued reference to FIG. 6, at procedure 620 of flow diagram 600, in various embodiments, a bottom electrode layer is deposited above the membrane layer. In some embodiments, the deposition is accomplished through deposition cycles. The bottom electrode layer may be similar to bottom electrodes BE1 and BE2 in FIG. 2B. The bottom electrode layer may be deposited and the gap may be created later, such as through patterning, etching, etc.

With continued reference to FIG. 6, at procedure 630 of flow diagram 600, in various embodiments, a piezoelectric layer is disposed above the bottom electrode layer. In some embodiments, the deposition is accomplished through deposition cycles. The piezoelectric layer may be similar to piezoelectric layer 203 of FIG. 2B. The piezoelectric layer may be deposited with a gap such that it is divided into piezoelectric portions 203-1 and 203-2 or the gap may be created later (if desired), such as through etching.

With continued reference to FIG. 6, at procedure 640 of flow diagram 600, in various embodiments, a top electrode layer is deposited above the piezoelectric layer. With reference to FIGS. 2A, 2B, and 2C the top electrode layer comprises a center electrode TE1, TE2 disposed above a center of the membrane layer 204 and a outer electrode TE3, TE4 spaced apart from the center electrode TE1, TE2. The segmented outer electrode (e.g., segments TE3 and TE4) is disposed such that it is spaced apart, away from the center of the membrane layer and around (i.e., surrounding except for the gaps) the segmented center electrode (e.g., around segments TE1 and TE2). In FIG. 2A, outer electrode segments TE3 and TE4 form a segmented circular ring around segments TE1 and TE2 of a circular center. However, in other transducer shapes (e.g., square, hexagonal, rectangular, oval) the segmented outer electrode as well as the center electrodes may have other shapes (e.g., square, hexagonal, rectangular, oval) and the segmented outer electrode forms a perimeter or periphery which is spaced apart and outward from the segmented center electrodes. Although the center electrode and outer electrode are each divided into two segments, following the same principles each may be divided into a larger number of segments. In some embodiments, the deposition is accomplished through deposition cycles. In some embodiments, the outer electrode and the center electrode are deposited such that they are substantially equal in surface area. In some embodiments, the top electrode layer may be deposited with gaps as illustrated in FIG. 2A such that the center electrode is divided into two portions TE1 and TE2 and the outer electrode is divided into two portions TE3 and TE4. In some embodiments, the gaps in the top electrode layer which are illustrated in FIG. 2A may be created later, after deposition, such as through etching. It should be appreciated that the gap between the segmented center electrodes TE1 and TE2 does not have to be aligned (i.e., on the same axis as the gaps between the outer electrode segments TE3 and TE4), and may be purposely misaligned in order to decrease the overall weakening of the transducer which may result by aligning all of the gaps on a single axis.

With continued reference to FIG. 6, at procedure 650 of flow diagram 600, in various embodiments, the top electrode layer, the piezoelectric layer, and the bottom electrode layer are etched. The creation of gaps may be accomplished via photolithographic patterning, etching, or lift-off. With reference to FIGS. 2A and 2B, the etching of the bottom electrode layer creates a first bottom electrode BE1 and a second bottom electrode BE2 from the bottom electrode layer. In some embodiments BE1 and BE 2 are equal or substantially equal in surface area. With reference to FIGS. 2A and 2B, the etching of the piezoelectric layer creates: a first piezoelectric portion 203-1 and a second piezoelectric portion 203-2 from the piezoelectric layer 203, where the first piezoelectric portion 203-1 disposed above the first bottom electrode BE1 and the second piezoelectric portion 203-2 disposed above the second bottom electrode BE2. With reference to FIGS. 2A and 2B, the etching of the top electrode layer creates a first outer electrode segment TE4 and a second outer electrode segment TE3 from the outer electrode, where the first outer electrode segment TE4 is disposed above the first bottom electrode BE1 and the second outer electrode segment TE3 is disposed above the second bottom electrode BE2. With reference to FIGS. 2A and 2B, the etching of the top electrode layer also creates a first center electrode segment TE1 and a second center electrode segment TE2 from the center electrode, where the first center electrode segment TE1 is disposed above the first bottom electrode BE1 and the second center electrode segment TE2 is disposed above the second bottom electrode BE2. In some embodiments the etching is accomplished to create the first center electrode segment TE1 and the second center electrode segment TE2 such that they are equal or substantially equal in surface area to the first outer electrode segment TE4 and the second outer electrode segment TE3. Put differently, the surface areas of TE1, TE2, TE3, and TE4 are equal or substantially equal.

Example Alternative Split-Electrode Piezoelectric Transducer

A variety of alternative arrangements of the layer stack-up of transducer 200A of FIGS. 2A and 2B are possible and anticipated. Some non-limiting examples of alternative designs include: 1) using the membrane layer itself as the bottom electrode BE, by doping portions of the membrane layer to make them conductive; 2) inverting the functionality of the bottom electrode and top electrode and with respect to FIGS. 2A and 2B and switching these layers in the stack-up (i.e., the top electrode would have two portions and the bottom electrode would have four portions); 3) inverting the order of the stack-up/layer ordering shown in FIGS. 2A and 2B (i.e., the top-to-bottom layer ordering becomes: membrane, bottom electrode layer, piezoelectric layer, and top electrode layer); and 4) placing the bottom electrode layer below the membrane layer.

FIG. 7A shows a top plan view of a split-electrode transducer 700, in accordance with various embodiments. This is a depiction of the second alternative example mentioned above. In some embodiments, split-electrode piezoelectric transducer 700 is an ultrasonic transducer and operates in the ultrasonic range. Except for the stack-up ordering which reverses the functionality of the top electrode layer and the bottom electrode layer, the operation and other characteristics are similar or the same as those described previously in conjunction with split-electrode transducer 200A. Section line B-B shows the position and direction of a side sectional view illustrated in FIG. 7B.

FIG. 7B shows a sectional side elevational view B-B of the split-electrode transducer 700 of FIG. 7A, in accordance with various embodiments.

With reference to FIGS. 7A and 7B, split-electrode piezoelectric transducer 700 includes: a top electrode a top electrode layer, TE; a bottom electrode layer, BE; a piezoelectric layer 203; and a membrane layer 204. In some embodiments, other layers such as protective layers, filler layers, and/or electrically insulating layers may be included. These other layers have not been depicted in order to improve clarity. It should be appreciated that membrane 204 moves up and down (relative to FIG. 7B) at a desired frequency to produce sound through the displacement of membrane 204, and that in FIG. 7B membrane 204 is depicted in a "displaced up" position of the transducer.

With continued reference to FIG. 7A, the BE layer comprises conductive material disposed above and coupled with the membrane layer 204 and it is split into at least four portions depicted as: a first bottom electrode BE1', a second bottom electrode BE2', a third bottom electrode BE3, and a fourth bottom electrode BE4. Bottom electrode layer BE comprises a segmented center electrode with segments BE1' and BE2' that are disposed above a center portion of the membrane layer 204 (in the same shape and fashion as TE1 and TE2 of FIG. 2A). Gap 702 shows the location of an electrical disconnect/gap between center electrode segments BE1' and BE2'. The bottom electrode layer BE also comprises a segmented outer electrode with segments BE3 and BE4 that are spaced apart, outward, from the segmented center electrode segments BE1' and BE2' (in the same fashion as TE3 and TE4 of FIG. 2A). In a circular embodiment, as depicted in FIGS. 7A and 7B, the outer electrode segments BE3 and BE4 are spaced radially outward, apart from the center electrode segments BE1' and BE2'. The segmented outer electrode (e.g., segments BE3 and BE4) is disposed such that it is spaced apart, away from the center of the membrane layer and around (i.e., surrounding except for the gaps) the segmented center electrode (e.g., around segments BE1' and BE2'). In FIG. 7A, outer electrode segments BE3 and BE4 form a segmented circular ring around segments TE1 and TE2 of a circular center. However, in other transducer shapes (e.g., square, hexagonal, rectangular, oval) the segmented ring as well as the center electrodes may have other shapes (e.g., square, hexagonal, rectangular, oval) and the segmented outer electrode forms a perimeter or periphery which is spaced apart and outward from the segmented center electrodes. Although the center electrode and outer electrode are each divided into two segments, following the same principles each may be divided into a larger number of segments. For example, each of the center electrode and the outer electrode may be divided into three segments, four segments, five segments six segments, etc. In some embodiments, each of the segments of the center electrode is equal or substantially equal (e.g., within manufacturing tolerances of a few percent) in surface area to one another. In some embodiments, each of the segments of the outer electrode is equal or substantially equal (e.g., within manufacturing tolerances of a few percent) in surface area to one another. In some embodiments, each of the individual segments of the segmented center electrode and of the segmented outer electrode is equal or substantially equal (e.g., within manufacturing tolerances of a few percent) in surface area to one another. That is, in some embodiments the plan view surface area of BE1'=the surface area of BE2'=the surface area of BE3=the surface area BE4.

It should be appreciated that electrical traces are required to be coupled to the electrodes in order to route various signals and/or provide various couplings (such as to another electrode, to ground, etc.), however in the interest of clarity these traces are not illustrated. Any suitable routing may be used for such these traces.

With continued reference to FIGS. 7A and 7B, a piezoelectric layer 203 is disposed above and coupled with the bottom electrode layer (i.e., bottom electrodes BE1', BE2', BE3, and BE4). In some embodiments, the piezoelectric layer 203 may comprise a first piezoelectric portion 203-1' disposed above BE2' and BE4 a second piezoelectric portion 203-2' disposed above BE1' and BE3.

With continued reference to FIGS. 7A and 7B, a top electrode layer TE comprised of conductive material is disposed above and coupled with the piezoelectric layer 203. The top electrode layer TE is split into at least two portions depicted as a first top electrode TE1', and a second top electrode TE2'. In some embodiments, the first top electrode TE1' and the second top electrode TE2' are substantially equal in surface area from a top plan view.

CONCLUSION

The examples set forth herein were presented in order to best explain, to describe particular applications, and to thereby enable those skilled in the art to make and use embodiments of the described examples. However, those skilled in the art will recognize that the foregoing description and examples have been presented for the purposes of illustration and example only. The description as set forth is not intended to be exhaustive or to limit the embodiments to the precise form disclosed. Rather, the specific features and acts described above are disclosed as example forms of implementing the claims.

Reference throughout this document to "one embodiment," "certain embodiments," "an embodiment," "various embodiments," "some embodiments," or similar term means that a particular feature, structure, or characteristic described in connection with the embodiment is included in at least one embodiment. Thus, the appearances of such phrases in various places throughout this specification are not necessarily all referring to the same embodiment. Furthermore, the particular features, structures, or characteristics of any embodiment may be combined in any suitable manner with one or more other features, structures, or characteristics of one or more other embodiments without limitation.

What is claimed is:

1. An ultrasonic transducer device comprising:
a piezoelectric micromachined ultrasonic transducer comprising:
  a membrane layer;
  a bottom electrode layer disposed above and coupled with the membrane layer and comprising a first bottom electrode and a second bottom electrode, wherein the first bottom electrode and the second bottom electrode are substantially equal in surface area;
  a piezoelectric layer disposed above and coupled with the bottom electrode layer and comprising a first piezoelectric portion disposed above the first bottom electrode and a second piezoelectric portion disposed above the second bottom electrode; and
  a top electrode layer disposed above and coupled with the piezoelectric layer and comprising a segmented center electrode disposed above a center of the membrane layer and a segmented outer electrode spaced apart from the segmented center electrode, wherein the segmented outer electrode is disposed away from the center of the membrane layer in a ring around the segmented center electrode, wherein a first segment of the segmented outer electrode and a first segment of the segmented center electrode are disposed above the first bottom electrode, wherein a second segment of the segmented outer electrode and a second segment of the segmented center electrode are disposed above the second bottom electrode, and wherein individual segments of the segmented center electrode and individual segments of the segmented outer electrode are all substantially equal in surface area;
a drive transmitter comprising a first output and a second output, wherein the first output and the second output are differential; and
a controller, responsive to the piezoelectric micromachined ultrasonic transducer being placed in a transmit mode, configured to electrically couple the first and second segments of the bottom electrode layer with ground, electrically couple the first output with the segments of the segmented center electrode, and to electrically couple the second output with the segments of the segmented outer electrode.

2. The ultrasonic transducer device of claim 1, further comprising:
a signal generator coupled to an input of the drive transmitter and configured to generate and provide a repeating waveform on the input.

3. The ultrasonic transducer device of claim 1, further comprising:
a charge pump coupled to the drive transmitter and configured to provide charge for amplifying an input to the drive transmitter.

4. The ultrasonic transducer device of claim 1, wherein the controller is configured to control a signal gain of the ultrasonic transducer device by controlling the coupling of the first and second bottom electrodes to ground.

5. The ultrasonic transducer device of claim 1, further comprising:
a front end amplifier comprising a first input and a second input, wherein the first input and the second input are differential; and
wherein, responsive to the piezoelectric micromachined ultrasonic transducer being switched from the transmit mode to a receive mode, the controller is configured to decouple the first and second bottom electrodes from ground, decouple the first and second outputs from the piezoelectric micromachined ultrasonic transducer, couple the first input with the first segment of the segmented outer electrode, couple the first segment of the segmented center electrode with ground, couple the second input with a second segment of the segmented center electrode, and couple the second segment of the segmented outer electrode with ground.

6. The ultrasonic transducer device of claim 5, wherein in response to the piezoelectric micromachined transducer being placed in the receive mode:
the first segment of the segmented outer electrode, the piezoelectric layer, and the first segment of the segmented center electrode form a first pair of series capacitors such that voltage received at the first input is substantially doubled by substantially halving a first capacitance associated with the first segment of the segmented center electrode; and
the second segment of the segmented outer electrode, the piezoelectric layer, and the second segment of the segmented center electrode form a second pair of series capacitors such that voltage received at the second input is substantially doubled by substantially halving a second capacitance associated with the second segment of the segmented center electrode.

7. The ultrasonic transducer device of claim 1, wherein, in response to the piezoelectric micromachined ultrasonic transducer being switched from a transmit mode to a receive mode, the controller is configured to decouple the first and second bottom electrodes from ground following a ringdown period of the piezoelectric micromachined ultrasonic transducer.

8. The ultrasonic transducer device of claim 7, wherein the ringdown period is at least as long as a transmit period immediately preceding the piezoelectric micromachined ultrasonic transducer being switched from the transmit mode to the receive mode.

9. The ultrasonic transducer device of claim 1, wherein: when, during operation, segments of the segmented center electrode present a concave surface disposed toward the membrane layer, segments of the segmented outer electrode present a convex surface oriented toward the membrane layer.

10. The ultrasonic transducer device of claim 1, wherein: the first piezoelectric portion and the second piezoelectric portion are substantially equal in surface area.

11. The ultrasonic transducer device of claim 1, wherein: the segmented center electrode is disposed above a portion of the piezoelectric layer in which a Laplacian of an out-of-plane displacement in the piezoelectric layer has a positive sign in a given displaced shape; and the segmented outer electrode is disposed above a second portion of the piezoelectric layer in which a Laplacian of the out-of-plane displacement in the piezoelectric layer has a negative sign in the same given displaced shape.

12. The ultrasonic transducer device of claim 1, wherein: the segmented center electrode is disposed above a portion of the piezoelectric layer in which a sum of the normal components of an in-plane strain in the piezoelectric layer has a positive sign in a given displaced shape; and the segmented outer electrode is disposed above a second portion of the piezoelectric layer in which a sum of the normal components of the in-plane strain in the piezoelectric layer has a negative sign in the same given displaced shape.

13. A piezoelectric micromachined transducer comprising:
a membrane layer;
a bottom electrode layer disposed above and coupled with the membrane layer and comprising a first bottom electrode and a second bottom electrode, wherein the first bottom electrode and the second bottom electrode are substantially equal in surface area;
a piezoelectric layer disposed above and coupled with the bottom electrode layer and comprising a first piezoelectric portion disposed above the first bottom electrode and a second piezoelectric portion disposed above the second bottom electrode, wherein the first piezoelectric portion and the second piezoelectric portion are substantially equal in surface area; and
a top electrode layer disposed above and coupled with the piezoelectric layer and comprising a segmented center electrode disposed above a center of the membrane layer and a segmented outer electrode spaced apart from the segmented center electrode, wherein the segmented outer electrode is disposed away from the center of the membrane layer in a ring around the segmented center electrode, wherein a first segment of the segmented outer electrode and a first segment of the segmented center electrode are disposed above the first bottom electrode, wherein a second segment of the segmented outer electrode and a second segment of the segmented center electrode are disposed above the second bottom electrode, and wherein individual segments of the segmented center electrode and individual segments of the segmented outer electrode are all substantially equal in surface area.

14. The piezoelectric micromachined transducer of claim 13, wherein:
of the center electrode segments and the outer electrode segments are positioned on the piezoelectric layer depending on a curvature of the piezoelectric layer.

15. The piezoelectric micromachined transducer of claim 13, wherein:
the segmented center electrode is disposed above a portion of the piezoelectric layer in which a Laplacian of an out-of-plane displacement in the piezoelectric layer has a positive sign in a given displaced shape; and
the segmented outer electrode is disposed above a second portion of the piezoelectric layer in which a Laplacian of the out-of-plane displacement in the piezoelectric layer has a negative sign in the same given displaced shape.

16. The piezoelectric micromachined transducer of claim 13, wherein:
the segmented center electrode is disposed above a portion of the piezoelectric layer in which a sum of the normal components of an in-plane strain in the piezoelectric layer has a positive sign in a given displaced shape; and
the segmented outer electrode is disposed above a second portion of the piezoelectric layer in which a sum of the normal components of the in-plane strain in the piezoelectric layer has a negative sign in the same given displaced shape.

17. A piezoelectric micromachined transducer comprising:
a membrane layer;
a bottom electrode layer disposed above and coupled with the membrane layer and comprising a first bottom electrode and a second bottom electrode, wherein the first bottom electrode and the second bottom electrode are substantially equal in surface area;
a piezoelectric layer disposed above and coupled with the bottom electrode layer and comprising a first piezoelectric portion disposed above the first bottom electrode and a second piezoelectric portion disposed above the second bottom electrode, wherein the first piezoelectric portion and the second piezoelectric portion are substantially equal in surface area; and
a top electrode layer disposed above and coupled with the piezoelectric layer and comprising a segmented first electrode disposed above a portion of the piezoelectric layer in which a Laplacian of an out-of-plane displacement in the portion of the piezoelectric layer has a positive sign in a given displaced shape, and a segmented second electrode spaced apart from the segmented first electrode and above second portion of the piezoelectric layer in which a Laplacian of the out-of-plane displacement in the second portion of the piezoelectric layer has a negative sign in the same given displaced shape, wherein a first segment of the segmented second electrode and a first segment of the segmented first electrode are disposed above the first bottom electrode, wherein a second segment of the segmented second electrode and a second segment of the segmented first electrode are disposed above the second bottom electrode, and wherein individual segments of the segmented first electrode and individual segments of the segmented second electrode are all substantially equal in surface.

18. A piezoelectric micromachined transducer comprising:
a membrane layer;
a bottom electrode layer disposed above and coupled with the membrane layer and comprising a first bottom electrode and a second bottom electrode, wherein the first bottom electrode and the second bottom electrode are substantially equal in surface area;
a piezoelectric layer disposed above and coupled with the bottom electrode layer and comprising a first piezoelectric portion disposed above the first bottom electrode and a second piezoelectric portion disposed above the second bottom electrode, wherein the first piezoelectric portion and the second piezoelectric portion are substantially equal in surface area; and
a top electrode layer disposed above and coupled with the piezoelectric layer and comprising a segmented first electrode disposed above a section of the membrane layer, in which a sum of the normal components of an in-plane strain in the piezoelectric layer has a positive sign in a given displaced shape, and a segmented second electrode spaced apart from the segmented first electrode, in which a sum of the normal components of the in-plane strain in the piezoelectric layer has a negative sign in the same given displaced shape, wherein a first segment of the segmented second electrode and a first segment of the segmented first electrode are disposed above the first bottom electrode, wherein a second segment of the segmented second electrode and a second segment of the segmented first electrode are disposed above the second bottom electrode, and wherein individual segments of the segmented first electrode and individual segments of the segmented second electrode are all substantially equal in surface area.

* * * * *

UNITED STATES PATENT AND TRADEMARK OFFICE
CERTIFICATE OF CORRECTION

| | |
|---|---|
| PATENT NO. | : 11,819,361 B2 |
| APPLICATION NO. | : 16/870929 |
| DATED | : November 21, 2023 |
| INVENTOR(S) | : Goericke et al. |

It is certified that error appears in the above-identified patent and that said Letters Patent is hereby corrected as shown below:

In the Claims

Column 22, Claim 14, Line 14:
Delete: "of"

Signed and Sealed this
Twenty-third Day of January, 2024

*Katherine Kelly Vidal*

Katherine Kelly Vidal
*Director of the United States Patent and Trademark Office*